US012311370B2

(12) United States Patent
Elf et al.

(10) Patent No.: US 12,311,370 B2
(45) Date of Patent: May 27, 2025

(54) MICROFLUIDIC DEVICE FOR CELL CHARACTERIZATION

(71) Applicant: ASTREGO DIAGNOSTICS AB, Uppsala (SE)

(72) Inventors: Johan Elf, Uppsala (SE); Ove Öhman, Uppsala (SE); Martin Lovmar, Mölndal (SE); Özden Baltekin, Uppsala (SE)

(73) Assignee: Astrego Diagnostics AB, Uppsala (SE)

(*) Notice: Subject to any disclaimer, the term of this patent is extended or adjusted under 35 U.S.C. 154(b) by 835 days.

(21) Appl. No.: 16/759,203

(22) PCT Filed: Oct. 30, 2018

(86) PCT No.: PCT/SE2018/051108

§ 371 (c)(1),
(2) Date: Apr. 24, 2020

(87) PCT Pub. No.: WO2019/088904

PCT Pub. Date: May 9, 2019

(65) Prior Publication Data

US 2020/0316600 A1 Oct. 8, 2020

(30) Foreign Application Priority Data

Oct. 31, 2017 (SE) .................................... 1751352-4

(51) Int. Cl.
*G01N 33/483* (2006.01)
*B01L 3/00* (2006.01)

(52) U.S. Cl.
CPC .... *B01L 3/502761* (2013.01); *G01N 33/4833* (2013.01); *B01L 2200/0652* (2013.01); *B01L 2300/0864* (2013.01); *B01L 2400/086* (2013.01)

(58) Field of Classification Search
CPC ....... B01L 3/502761; B01L 2200/0652; B01L 2300/0864; B01L 2400/086; G01N 33/4833
See application file for complete search history.

(56) References Cited

U.S. PATENT DOCUMENTS

| | | | |
|---|---|---|---|
| 8,372,629 | B2 | 2/2013 | Southern et al. |
| 9,188,586 | B2 | 11/2015 | Fan et al. |
| 9,304,065 | B2 | 4/2016 | Fowler et al. |
| 9,429,500 | B2 | 8/2016 | Fowler et al. |
| 9,506,845 | B2 | 11/2016 | Fowler et al. |
| 9,506,917 | B2 | 11/2016 | Fan et al. |
| 9,952,126 | B2 | 4/2018 | Fowler et al. |
| 10,274,486 | B2 | 4/2019 | Fan et al. |
| 10,983,116 | B2 | 4/2021 | Fan et al. |
| 2003/0044389 | A1 | 3/2003 | Brown et al. |
| 2009/0098541 | A1 | 4/2009 | Southern et al. |
| 2013/0190202 | A1 | 7/2013 | Southern et al. |
| 2013/0295602 | A1 | 11/2013 | Fowler et al. |
| 2013/0296196 | A1 | 11/2013 | Fowler et al. |
| 2013/0302807 | A1 | 11/2013 | Fowler et al. |
| 2013/0302883 | A1 | 11/2013 | Fowler et al. |
| 2013/0302884 | A1 | 11/2013 | Fowler et al. |
| 2015/0204862 | A1 | 7/2015 | Fan et al. |
| 2015/0204864 | A1 | 7/2015 | Fan et al. |
| 2017/0067887 | A1 | 3/2017 | Fan et al. |
| 2017/0137861 | A1 | 5/2017 | Elf et al. |
| 2018/0015470 | A1 | 1/2018 | Chen et al. |
| 2018/0306683 | A1 | 10/2018 | Fowler et al. |
| 2019/0324028 | A1 | 10/2019 | Fan et al. |
| 2022/0057388 | A1 | 2/2022 | Fan et al. |

FOREIGN PATENT DOCUMENTS

| | | | |
|---|---|---|---|
| CN | 101208421 | A | 6/2008 |
| CN | 104884605 | A | 9/2015 |
| CN | 107206380 | A | 9/2017 |
| WO | 2010/108003 | A2 | 9/2010 |
| WO | 2013/130714 | A1 | 9/2013 |
| WO | 2015/145280 | A1 | 10/2015 |
| WO | 2016/007068 | A1 | 1/2016 |
| WO | 2018/174784 | A1 | 9/2018 |

OTHER PUBLICATIONS

Office Action from corresponding Japanese Application No. 2020-522948 dated Aug. 2, 2022 with English Translation.
Search Report from corresponding CN Application No. 218800699046 dated Dec. 3, 2023.
Baltekin, Özden et al., Fast Antibiotic Susceptibility Testing (FASTest) based on single cell growth rate measurements, bioRxiv, doi: https://doi.org/10.1101/071407, pp. 1-16 (Aug. 2016).
Kastania, Athina S. et al., Binding kinetics of bacteria cells on immobilized antibodies in microfluidic channels Modeling and experiments, Sensors and Actuators B: Chemical, vol. 253, pp. 247-257 (Online Jun. 19, 2017).
Baltekin, Özden et al., Antibiotic susceptibility testing in less than 30 min using direct single cell imaging, PNAS, 114(34): 9170-9175 (Online Aug. 8, 2017).
Kim, Samuel et al., Miniaturized Antimicrobial Susceptibility Test by Combining Concentration Gradient Generation and Rapid Cell Culturing. Antibiotics 4: 455-466 (2015).

*Primary Examiner* — Elizabeth C. Kemmerer
*Assistant Examiner* — McKenzie A Dunn
(74) *Attorney, Agent, or Firm* — Porter Wright Morris & Arthur LLP

(57) ABSTRACT

A microfluidic device (1) comprises a substrate (10) having spatially defined and separated cell compartments (20) configured to accommodate cells. A respective first end (22) of the spatially defined and separated cell compartments (20) is in fluid connection with a flow input channel (30). The microfluidic device (1) comprises at least one identification surface (60, 61) comprising immobilized affinity molecules configured to capture cells of a species or serotype or of a group of species or serotypes.

19 Claims, 18 Drawing Sheets

MICROFLUIDIC DEVICE FOR CELL CHARACTERIZATION

TECHNICAL FIELD

The present embodiments generally relate to a microfluidic device, and in particular to such a microfluidic device useful in characterizing cells.

BACKGROUND

With the ever-increasing emergence and spread of antibiotic resistant bacteria, a key factor in correct treatment of infections is the ability to rapidly and robustly identify the cause of the infection in order to select appropriate treatment. If bacteria are detected it is important to identify the infecting species and its antibiotic susceptibility profile in order to assure the use of an efficacious antibiotic and reduce the need for broad-spectrum drugs. Currently, a bacterial pathogen's resistance to an antibiotic is detected either by phenotyping in the absence and presence of the antibiotic, or by genotyping for the genetic markers correlated with previously observed phenotypic resistance.

Phenotypic antibiotic susceptibility tests (ASTs) are typically based on the detection of differential bacterial growth with and without antibiotics in liquid cultures or on solid agar plates. In liquid tests, detection is based on the change in optical density, while the disk diffusion method is used on solid agar plates to identify inhibition zones. These methods are generally reliable for detecting resistance and determining the antibiotic concentration that halts bacterial growth, making them predictive of the therapeutic utility of different antibiotics. However, since it takes 1-2 days to get a reliable readout, these methods fail to provide information on how to treat a patient in the often critical, early infection stages. As a consequence, the physician is left with the difficult choice of prescribing a broad spectrum antibiotic or risking that the first prescribed antibiotic will be ineffective.

Genotypic ASTs are based on detection of specific genetic markers, such as plasmids, genes or mutations, associated with resistance phenotypes by using common genetic tools, e.g., sequence specific amplification by polymerase chain reaction (PCR), by padlock probe mediated rolling circle amplification (RCA) or whole genome sequencing. These tests are highly sensitive and can limit the detection time to what is needed to amplify selected DNA sequences to detectable levels. However, they require advance knowledge of which resistance markers to test for. If new resistance mechanisms arise, these would go undetected and result in false negatives. Furthermore, presence of certain resistance genes and/or mutations does not necessarily translate into phenotypic resistance.

Unlike the genotypic ASTs, the phenotypic ASTs directly assess if the antibiotic stops bacterial growth, which is the most relevant measure for the treating physician. New phenotypic ASTs have therefore been developed in recent years to decrease the detection time.

By detecting the relative abundance of 16S rRNA in liquid cultures instead of measuring optical density, the AST detection time can be pushed down to a few hours. Similarly, by reducing the growth volume and applying z-stack imaging to calculate the cell occupancy, the detection time for AST was decreased to ~100 min. Over the last few years, microfluidics has revolutionized microbial single cell manipulation and observation, and a fruitful direction for AST is to use microfluidics to miniaturize the bacterial incubation chambers to increase the signal to background ratio. One recent example of a simple microfluidic based AST method creates a concentration gradient and applies it to small cell cultures in 30 nL chambers. Analysis of images taken every 60 min allow for detection of the minimum inhibitory concentration (MIC) in 180 min [1].

One restriction in making effective microfluidics based ASTs has been the difficulty in capturing or loading cells into the microfluidic devices. One solution is to load bacteria liquid culture mixed with liquid agarose, which solidifies upon cooling and captures the bacteria. In this approach, delivery of the antibiotic to the microfluidic agarose channel (MAC) relies on diffusion, and fast AST, typically 1-4 hours, is achieved by tracking the single cell growth rate from phase contrast images. Another solution builds on the success of MAC by moving it to a 96-well chip and combining it with single cell morphological analysis (SCMA). This method allows simultaneous identification of various responses of multiple species to various antibiotics and was able to detect Methicillin resistant *Staphylococcus aureus* within 60-120 min.

A microfluidic device that can be used for phenotypic characterization of cells has been developed [2]. The microfluidic device comprises a plurality of parallel cell channels having a respective first end in fluid connection with a flow input channel and a respective second end in fluid connection with a first end of a respective wash channel. The respective second end of the wash channels is in fluid connection with a flow output channel. The cell channels have dimensions to accommodate cells, whereas the wash channels have dimensions too small to accommodate the cells.

The microfluidic device as disclosed in [2] was used to make an AST faster than 30 min starting with only a thousand bacterial cells in less than 1 mL of liquid [3]. The fast AST is based on a microfluidic capturing technique and single cell growth rate measurements.

Single-cell capturing and processing utilizing microfluidics is disclosed in [4]. Individual cells are captured and partitioned from a larger population of cells along with generating genetic information and/or reactions related to each individual cell.

There is still a need for improvements within the field of cell characterization using microfluidic devices.

SUMMARY

It is a general objective to enable cell characterization using microfluidic devices.

This and other objectives are met by embodiments as disclosed herein.

An aspect of the embodiments relates to a microfluidic device comprising a substrate having spatially defined and separated cell compartments configured to accommodate cells. A respective first end of the spatially defined and separated cell compartments is in fluid connection with a flow input channel. The microfluidic device comprises at least one identification surface comprising immobilized affinity molecules configured to capture cells of a species or serotype or of a group of species or serotypes.

Another aspect of the embodiments relates to a method of characterizing cells. The method comprises loading a biological sample comprising cells into a microfluidic device according to above to capture cells in the spatially defined and separated cell compartments. The method also comprises exposing cells in the spatially defined and separated cell compartments to a test agent and monitoring cells in the spatially defined and separated cell compartments. The method further comprises determining a phenotypic response of cells to the test agent based on monitoring the cells in the spatially defined and separated cell compartments. The method additionally comprises determining a species or serotype or a group of species or serotypes based on presence of cells captured by the affinity molecules immobilized onto the at least one identification surface.

The present embodiments achieve a biologically relevant classification of cells in a biological sample by not only determining the phenotypic response of the cells but additionally identifying the species or serotype of the cells.

BRIEF DESCRIPTION OF THE DRAWINGS

The embodiments, together with further objects and advantages thereof, may best be understood by making reference to the following description taken together with the accompanying drawings, in which.

DETAILED DESCRIPTION

Figure 1:
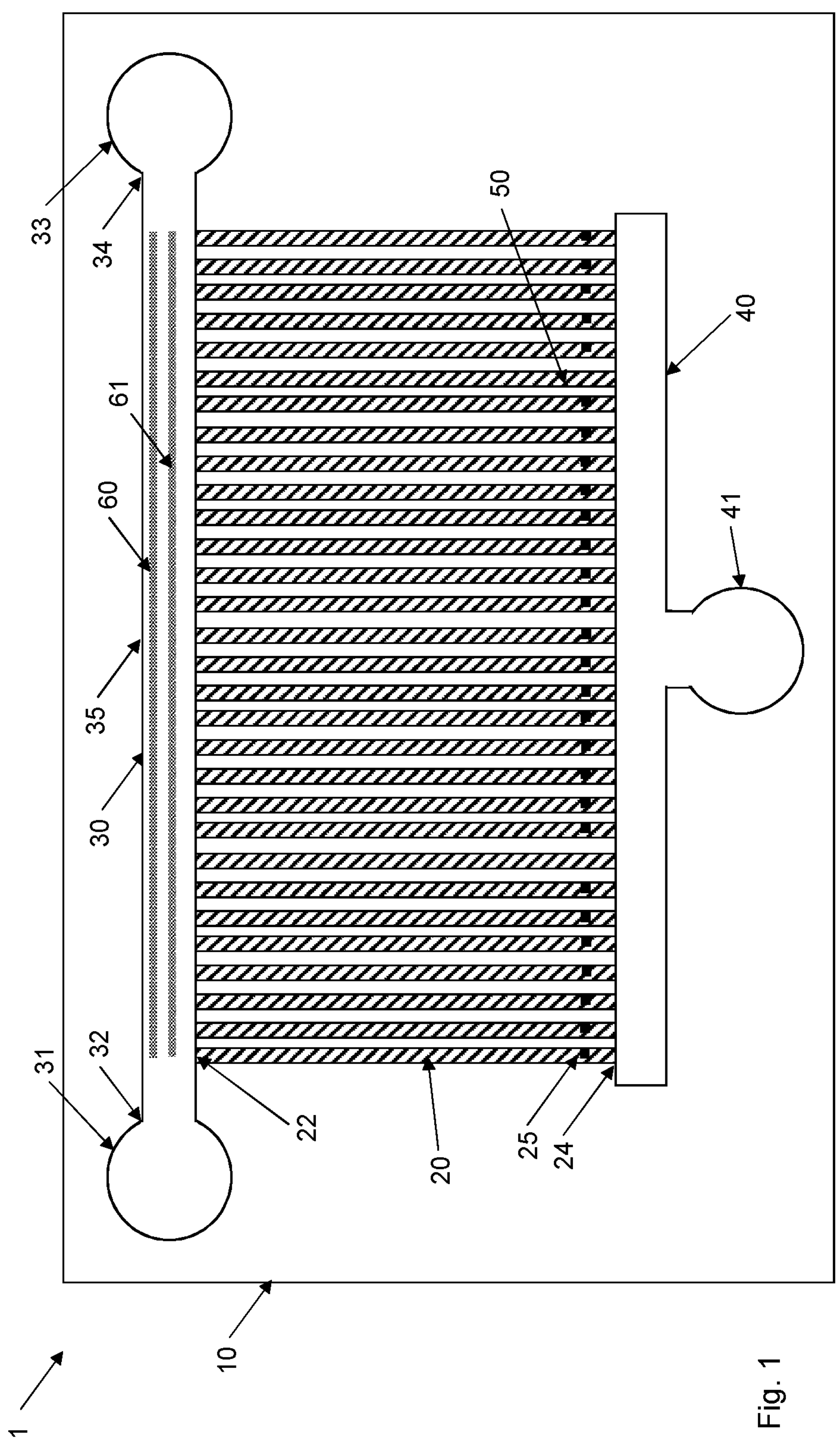
FIG. 1 is an illustration of a microfluidic device according to an embodiment.

Throughout the drawings, the same reference numbers are used for similar or corresponding elements.

The present embodiments generally relate to a microfluidic device, and in particular to such a microfluidic device useful in characterizing cells.

The microfluidic device according to the embodiments constitutes an efficient means of characterizing cells in a sample. Such a microfluidic device, also denoted microfluidic chip in the art, can be used for phenotyping, i.e., phenotypic characterization, of cells in a time efficient way. However, in real-life applications the biological sample input to the microfluidic devices can be a complex and heterogeneous sample comprising various biological material including target cells to be phenotyped, other cells and cellular debris, and non-biological material, such as dirt, contaminants, etc. Hence, the biological sample is most often heterogeneous and the target cells may in fact constitute a minority, even a minute minority, of the material present in the biological sample.

It is therefore a general need for not only characterizing cells in terms of phenotyping cells but also determine the species or serotype of cells in the biological sample. Information of species or serotype may be useful in interpretation of phenotypic data in order to obtain a more complete and correct classification of cells in the biological sample. For instance, complementing phenotypic data in terms of antibiotic susceptibility testing (AST) data of bacteria in a biological sample, such as a urine sample or a blood sample, with identification of species or serotype data enables a more accurate treatment strategy to combat or treat a bacterial infection, such as urine tract infection (UTI) or sepsis.

An aspect of the embodiments relates to a microfluidic device comprising a substrate having spatially defined and separated cell compartments configured to accommodate cells. A respective first end of the spatially defined and separated cell compartments is in fluid connection with a flow input channel. According to the embodiments, the microfluidic device comprises at least one identification surface comprising immobilized affinity molecules configured to capture cells of a species or serotype or of a group of species or serotypes.

The microfluidic device of the embodiments thereby comprises a substrate with spatially defined and separated cell compartments defined therein. These spatially defined and separated cell compartments are configured to and thereby have a dimension configured or designed to accommodate cells. Such cell compartments are designed to capture and house cells present in a biological sample, i.e., a sample comprising cells. Accordingly, when loading the biological sample into the microfluidic device cells present in the biological sample are captured by the cell compartments. The cell compartments are spatially defined and separated. This means that each cell compartment has a spatially defined position in the microfluidic device and in the substrate and each cell compartment is separated, typically physically separated, from other cell compartments in the microfluidic device. Accordingly, it is possible to physically separate and individually monitor cells in the spatially defined and separated cell compartments of the microfluidic device.

The microfluidic device comprises at least one identification surface comprising immobilized affinity molecules. These affinity molecules are configured to capture cells present in the biological sample. In more detail, the affinity molecules are used to capture cells of a given species, of a given serotype, of a given group of species or of a given group of serotypes.

A serotype or serovar is a distinct variation within a species of cells, such as bacteria. These cells are classified together based on their cell surface antigens, allowing the epidemiologic classification of organisms to the sub-species level. A group of serotypes with common antigens is called a serogroup or sometimes serocomplex.

A group of species could, with regard to cells in a biological sample, constitute a genus comprising multiple, i.e., at least two, species. Also other groups of species could be captured by affinity molecules immobilized onto the substrate in the microfluidic device. Typical example of such a group of species include gram-positive bacteria, gram-negative bacteria, etc.

Various examples of microfluidic devices according to various embodiments will now be described in more detail with reference to the drawings.

FIG. 1 is a schematic illustration of a microfluidic device 1 according to an embodiment. The microfluidic device 1 comprises a substrate 10 having spatially defined and separated cell compartments 20 configured to accommodate cells. A respective first end 22 of the spatially defined and separated cell compartments 20 is in fluid connection with a flow input channel 30 having a first end 32 in fluid connection with a first fluid port 31 and a second end 34 in fluid connection with a second fluid port 33. A respective second end 24 of the spatially defined and separated cell compartments 20 is in fluid connection with a flow output channel 40 in fluid connection with a third fluid port 41. The spatially defined and separated cell compartments 20 comprise a respective obstruction 25 designed to prevent selected cells, such as of a particular size, dimension, shape, form or rigidity/elasticity, from passing the respective obstruction 25 and into the flow output channel 40.

The embodiment illustrated in FIG. 1 comprises spatially defined and separated cell compartments 20 in the form of cell channels 20 arranged substantially parallel between the flow input channel 30 and the flow output channel 40.

The obstruction 25 provided in the cell channels 20, preferably at or in connection with the second end 24 of the cell channels 20, could be any physical obstruction or structure preventing selected cells entering the first end 22 of the cell channels 20 from the flow input channel 30 from passing out through the second end 24 of the cell channels 20 and into the flow output channel 40. Thus, the obstruction 25 effectively traps the selected cells in the cell channels 20.

The obstruction 25 may be in the form of a restriction or obstruction restricting the dimension, such as width and/or height, of the spatially defined and separated cell channels 20. This restriction or obstruction will thereby prevent selected cells having size larger than the restricted width and/or height from passing the obstruction 25. However, smaller cells and biological and non-biological material having a size smaller than the restricted width and/or height can pass the obstruction 25 and will thereby washed out into the flow output channel 40 and the third fluid port 41.

Depending on the design of the obstruction 25, the selection of which objects, such as cells, that are allowed to pass the obstruction 25 and which objects that become trapped in the cell channels 20 could be based on the size of the object, such as length, width, height, diameter, etc.; the shape or form of the object; but also other characteristics of the object, such as deformability, elasticity or rigidity allowing the object to be deformed and flushed past the obstruction 25 by a fluid flow through the cell channels 20.

The microfluidic device 1 also comprises at least one identification surface 60, 61 comprising immobilized affinity molecules. In an embodiment, the at least one identification surface 60, 61 is at least one surface of the substrate 10. In a particular example of such an embodiment, the at least one identification surface 60, 61 is at least one surface of the flow input channel 30. In FIG. 1, the at least one identification surface 60, 61 has been exemplified by at least one elongated surface extending substantially over the complete length of the flow input channel 30. In more detail, the flow input channel 30 comprises an intermediate channel portion 35 provided between the first end 32 in fluid connection with the first fluid port 31 and the second end 34 in fluid connection with the second port 33. The respective first end 22 of the spatially defined and separated cell channels 20 is in fluid connection with the intermediate channel portion 35. The at least one identification surface 60, 61 may then be at least one surface of the intermediate channel portion 35.

In FIG. 1, the at least one identification surface 60, 61 is an elongated surface extending substantially over the complete length of the intermediate channel portion 35. This should merely be seen as an illustrative example. The at least one identification surface 60, 61 could alternatively extend over merely a part of the length of the intermediate channel portion 35, a part or the complete width of the intermediate channel portion 35 or indeed any sub-portion of the surface of the intermediate channel portion 35.

Figure 2:
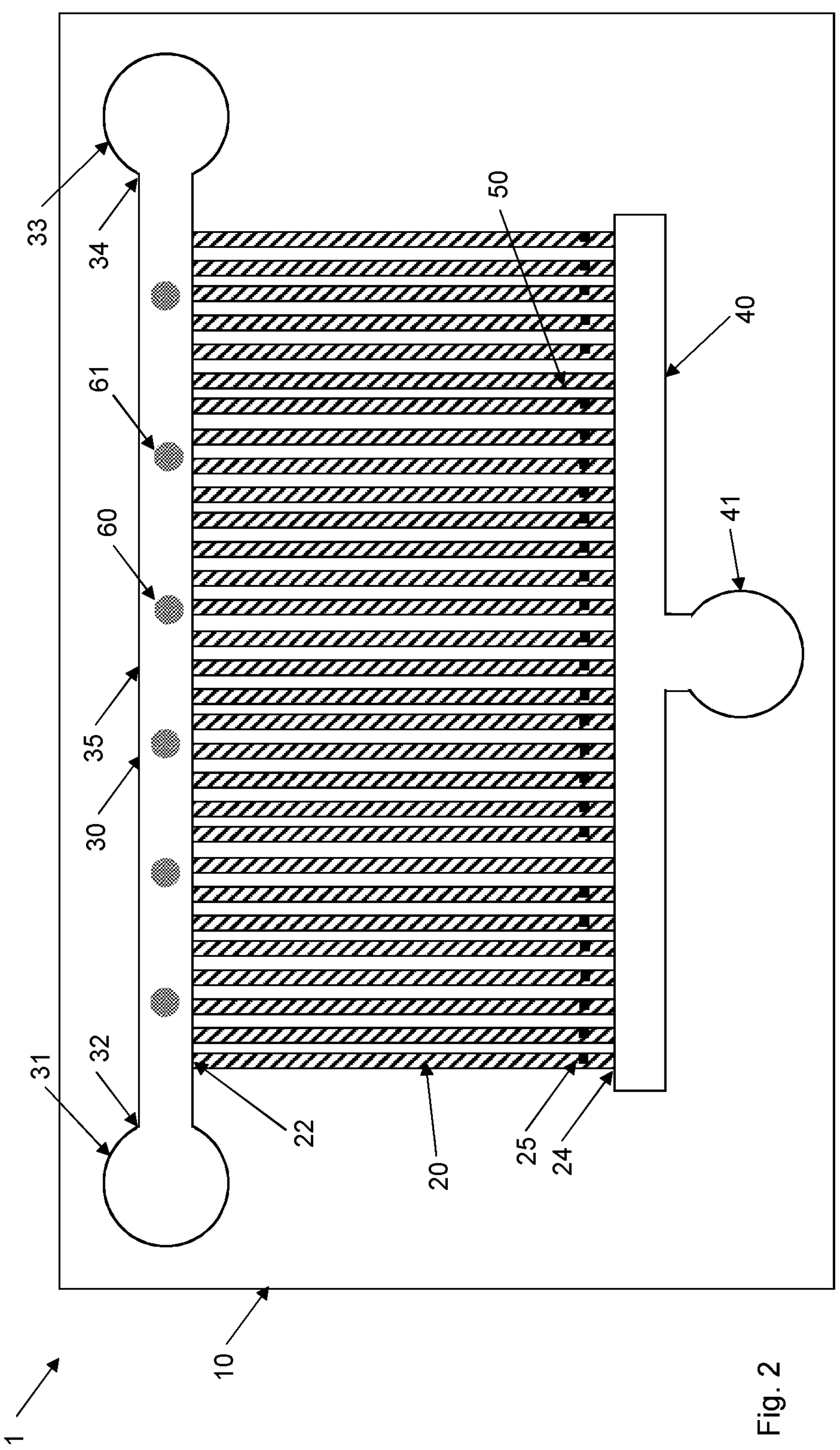
FIG. 2 is an illustration of a microfluidic device according to another embodiment.

FIG. 2 schematically illustrates such an alternative. In this embodiment, affinity molecules are distributed in multiple respective identification surfaces 60, 61 along the length of the intermediate channel portion 35. The respective identification surface 60, 61 has, as an illustrative but non-limiting example, a general circular shape in the surface of the intermediate channel portion 35.

Generally, during use of the microfluidic devices 1 as shown in FIGS. 1 and 2, a biological sample is loaded into the first fluid port 31 allowing excessive biological sample to flow out through the third fluid port 41 and optionally the second fluid port 33 to capture cells in the spatially defined and separated cell channels 20 by the obstructions 25.

Thus, the biological sample is input into the first fluid port 31 and is allowed to flow through the flow input channel 30 preferably towards and optionally out from the second fluid port 33. In addition, the biological sample including the cells will flow into the spatially defined and separated cell channels 20 and further into the flow output channel 40 and the third fluid port 41.

The spatially defined and separated cell channels 20 are dimensioned, i.e., having size, such as width and height, and shape, to allow selected cells to enter the spatially defined and separated cell channels 20. Cells or non-cell material having a size and/or shape that is too big or not adapted to the cross-sectional size and shape of the spatially defined and separated cell channels 20 will not enter the cell channels 20 but rather flow out from the flow input channel 30 through the second fluid port 33.

The obstruction 25 of the spatially defined and separated cell channels 20 is designed to have a shape and dimension, such as width and/or height, that prevent the selected cells from passing the obstruction 25 and enter the flow output channel 40. Accordingly, the selected cells will become trapped and captured in the cell channels 20.

Furthermore, cells present in the biological sample are captured by affinity molecules in the at least one identification surface 60, 61. Accordingly, cells, for which the affinity molecules have affinity, become captured and immobilized in the at least one identification surface 60, 61 in the intermediate channel portion 35. In this embodiment, the capture of cells in the at least one identification surface 60, 61 is thereby preferably performed in connection with loading of the biological sample into the first fluid port 31.

Only cells expressing and presenting molecules for which the affinity molecules have affinity or for which secondary affinity molecules have affinity, which will be described further herein, are captured at the at least one identification surface 60, 61. Other cells or material present in the biological sample will thereby not be captured by the affinity molecules. This means that the capture and presence of cells in at least one of the identification surfaces 60, 61 is an indication of the presence of cells of a given species or serotype or of a given group of species or serotypes in the biological sample.

Figure 3:
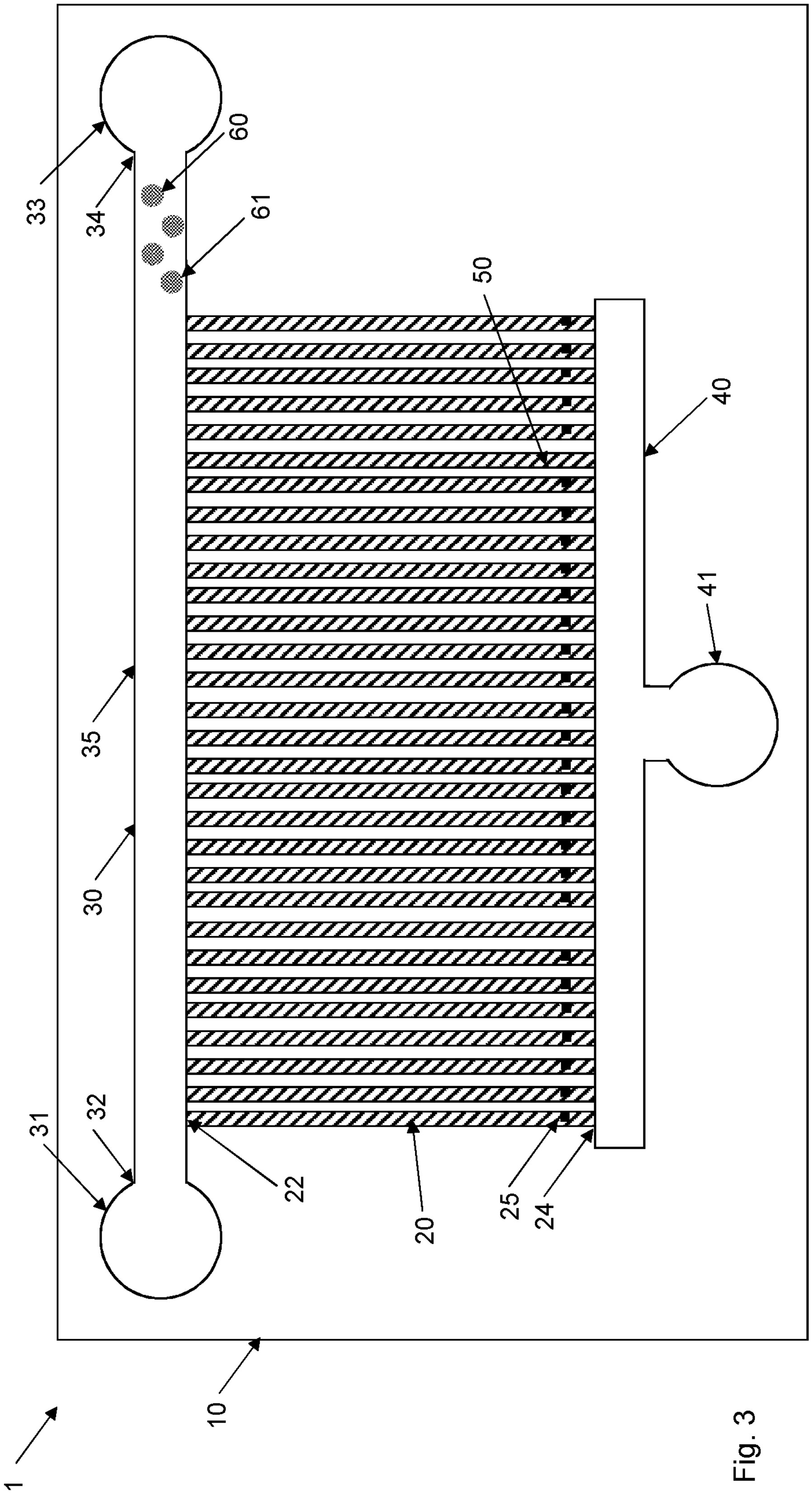
FIG. 3 is an illustration of a microfluidic device according to a further embodiment.

FIG. 3 is a schematic illustration of a microfluidic device 1 according to another embodiment. In this embodiment, the at least one identification surface 60, 61 is at least one surface of the flow input channel 30 at a position between the intermediate channel portion 35 and the second end 34 of the flow input channel 30.

In this embodiment, the at least one identification surface 60, 61 is arranged at surface of the flow input channel 30 downstream of the intermediate channel portion 35, to which the respective first ends 22 of the cell channels 20 are in fluid connection, when assuming a fluid flow from the first fluid port 31 towards the second fluid port 33 and/or the third fluid port 41. At this position, the at least one identification surface 60, 61 and any cells captured thereon will not block or obstruct the entrance to any cell channels 20, i.e., will not interfere with the entry of cells into any cell channel 20 through the first end 22.

In another embodiment, the at least one identification surface 60, 61 is at least one surface of the flow input channel 30 at a position between the intermediate channel portion 35 and the first end 32 of the flow input channel 30. Thus, in this embodiment the at least one identification surface 60, 61 is arranged at surface of the flow input channel 30 upstream of the intermediate channel portion 35, when assuming a fluid flow from the first fluid port 31 towards the second fluid port 33 and/or the third fluid port 41.

Figure 4:
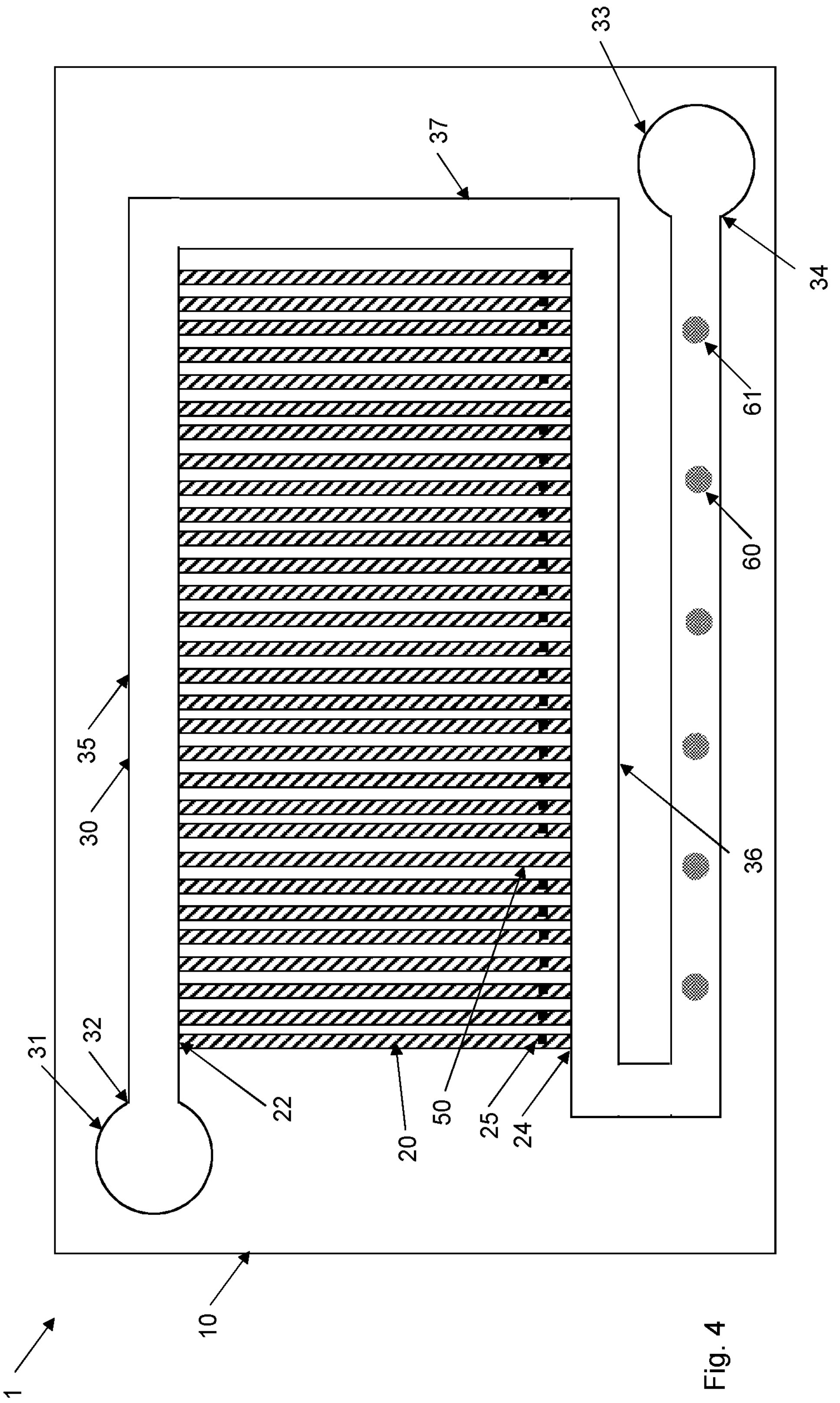
FIG. 4 is an illustration of a microfluidic device according to yet another embodiment.
Figure 5:
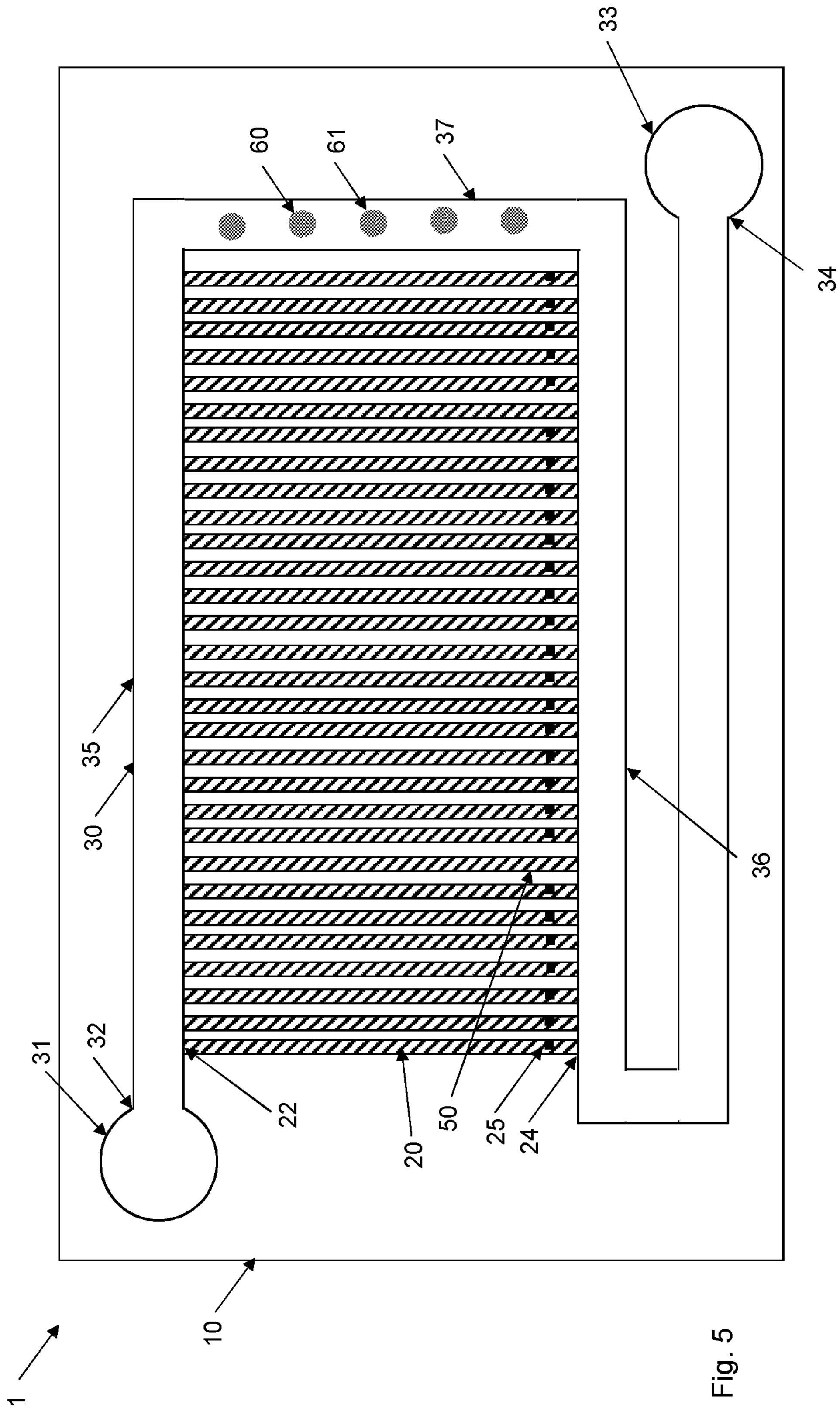
FIG. 5 is an illustration of a microfluidic device according to an embodiment.

FIGS. 4 and 5 illustrate further embodiments of the microfluidic device 1. In these embodiments the flow input channel 30 comprises the first end 32 in fluid connection with the first fluid port 31 and the second end 34 in fluid connection with the second fluid port 33. The flow input channel 30 also comprises a first intermediate channel portion 35 and a second intermediate channel portion 36. The respective first end 22 of the spatially defined and separated cell channels 20 is in fluid connection with the first intermediate channel portion 35 and the respective second end 24 of the spatially defined and separated cell channels 20 is in fluid connection with the second intermediate channel portion 36. Thus, the first intermediate channel portion 35 is provided between the first end 32 of the flow input channel 30 and the second intermediate channel portion 36 and the second intermediate channel portion 36 is provided between the first intermediate channel portion 35 and the second end 34 of the flow input channel 30.

In the embodiment illustrated in FIG. 4, the at least one identification surface 60, 61 is at least one surface of the flow input channel 30 at a position between the second intermediate channel portion 36 and the second end 34 of the flow input channel 30.

In the embodiment in FIG. 5 the at least one identification surface 60, 61 is at least one surface of the flow input channel 30 at a position 37 between the first intermediate channel portion 35 and the second intermediate channel portion 36.

The two embodiments described above in connection with FIGS. 4 and 5 lack the separate flow output channel and third port of the embodiments shown in FIGS. 1-3. In clear contrast, the flow input channel 30 extends between the first and second ends 22, 24 of the cell channels and thereby operates both as an input channel and an output channel. This means that the biological sample is loaded into the first fluid input 31 flows through the first intermediate channel portion 35 both through the cell channels 20 and the portion or the connection 37 between the first and second intermediate channel portions 35, 36 into the second intermediate channel portion 36 and then further out through the second fluid port 33.

FIGS. 4 and 5 show positions of the at least one identification surfaces 60, 61 that are beyond the portions of the flow input channel 30 connected to the ends 22, 24 of the cell channels, i.e., the first and second intermediate channel portions 35, 36.

The design of the flow input channel 30 according to FIGS. 4 and 5 can also be used in connection with other placements of the at least one identification surface 60, 61, such as between the first end 32 of the flow input channel 30 and the first intermediate channel portion 35, at the first intermediate channel portion 35 and/or at the second intermediate channel portion 36.

Figure 6:
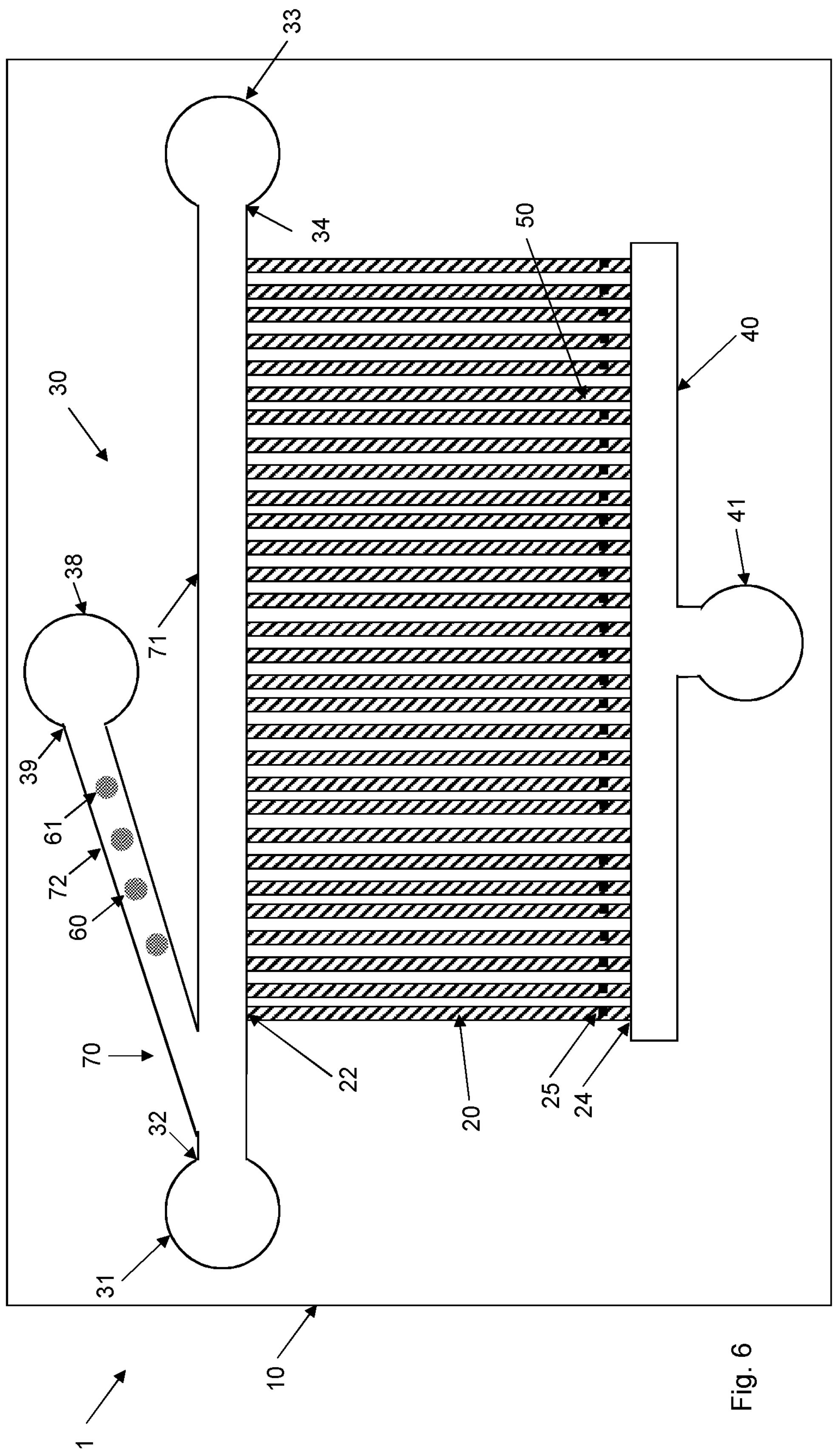
FIG. 6 is an illustration of a microfluidic device according to another embodiment.

FIG. 6 schematically illustrates yet another embodiment of the microfluidic device 1. In this embodiment, the flow input channel 30 comprises the first end 32 in fluid connection with the first fluid port 31 and a channel branch 70. The channel branch 70 divides the flow input channel 30 into at least a first flow input sub-channel 71 having a second end 34 in fluid connection with the second fluid port 33 and a second flow input sub-channel 72 having a second end 39 in fluid connection with a fourth fluid port 38. The respective first end 22 of the spatially defined and separated cell channels 20 is in fluid connection with the first flow input sub-channel 71. The at least one identification surface 60, 61 is at least one surface of the second flow input sub-channel 72.

This means that the flow input channel 20 branches or divides into multiple flow input sub-channels 71, 72. In such a case, one 71 of these flow input sub-channels 71, 72 is in fluid connection with the cell channels 20 and the second fluid port 33, whereas another 72 of the flow input sub-channels 71, 72 comprises the at least one identification surface 60, 61 and is connected to the fourth fluid port 38.

A biological sample 31 loaded into the first fluid port 31 may therefore be divided at the channel branch 70 to partly flow into the first flow input sub-channel 71 and partly flow into the second flow input sub-channel 72. Alternatively, the loading of the biological sample can be controlled in such a way to direct the biological sample first into the second flow input sub-channel 72 and then into the first flow input sub-channel 71 or vice versa. In either case, cells present in the biological sample may be captured by affinity molecules in the at least one identification surface 60, 61, whereas other cells enter the cell channels 20.

It is of course possible to have the channel branch 70 at other positions in the flow input channel 30 between the first end 32 and the second end 34 thereof. For instance, the channel branch 70 could be provided at a position of the flow input channel 30 between the intermediate channel portion and the second end 34 or indeed at any position along the intermediate channel portion.

FIG. 6 illustrates an embodiment where the channel branch 70 is taking place in the substrate 10 of the microfluidic device 1. In an alternative embodiment, the channel branch 70 could be arranged outside of the substrate 10. In such a case, the first fluid port 31 is also present outside of the substrate 10. For instance, a tube is connected to the external first fluid port 31 and is branched into two downstream tubes. One of these downstream tubes is in fluid connection with the first flow input sub-channel 71, whereas the other downstream tube is in fluid connection with the second flow input sub-channel 72. The two flow input sub-channels 71, 72 may then be arranged in the same substrate 10 or in different substrates. In the latter case, the microfluidic device 1 thereby comprises a first substrate comprising the first flow input sub-channel 71, the cell channels 20 and preferably the flow output channel 40, and optionally the second fluid port 33 and the third fluid port 41. The second substrate then comprises the second flow input sub-channel 72 with the at least one identification surface 60, 61 and optionally the fourth fluid port 38.

Figure 7:
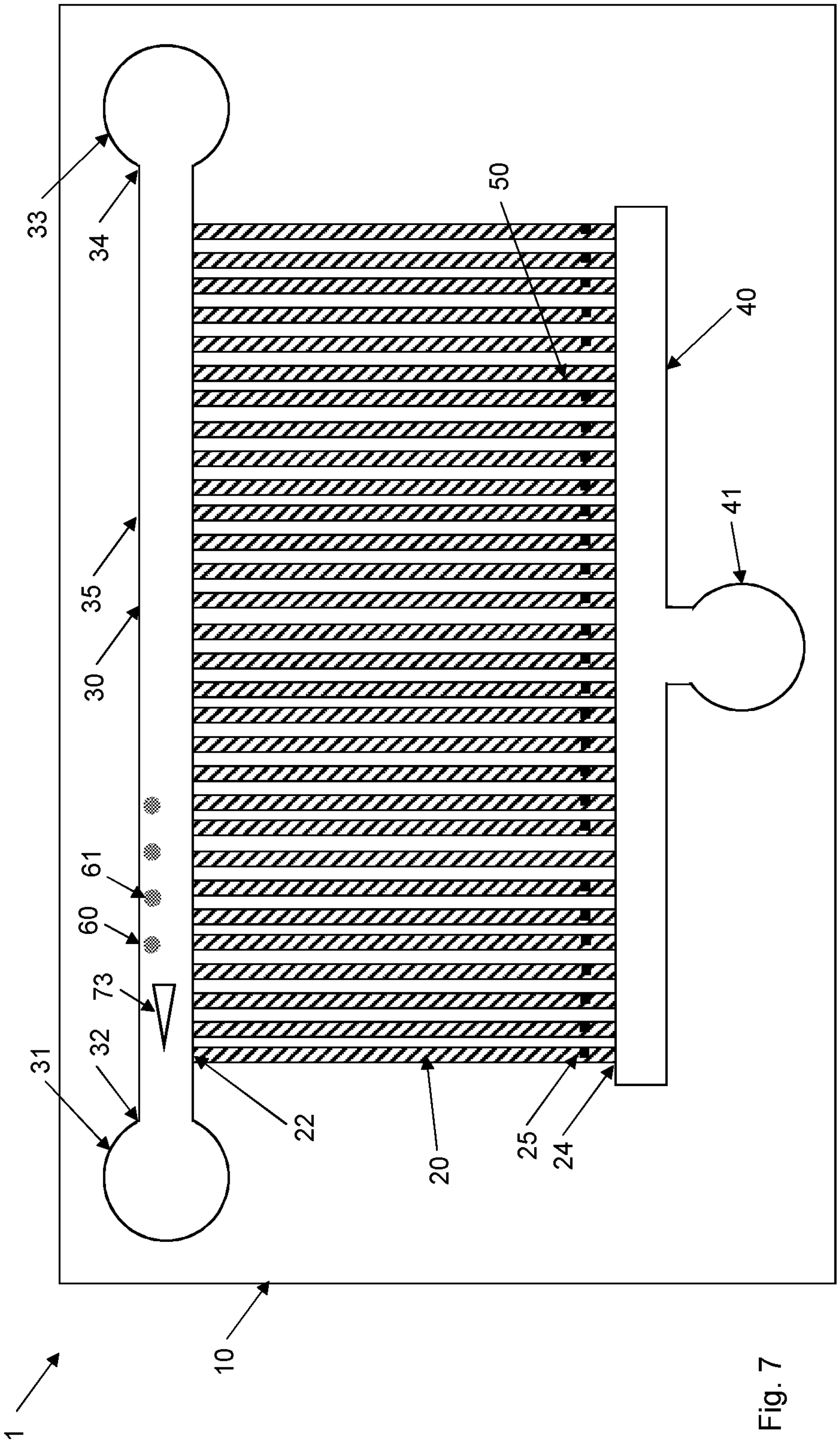
FIG. 7 is an illustration of a microfluidic device according to a further embodiment.

In an embodiment, see FIG. 7, the microfluidic device 1 comprises at least one flow guide 73 configured to guide at least a portion of a flow through the flow input channel 30 over the at least one identification surface 60, 61.

25 In FIG. 7, the flow guide 73 has been exemplified by a wedge 73 arranged in the flow input channel 30 to guide a portion of the flow through the flow input channel 30 over the at least one identification surface 60, 61. At the same time the wedge is able to guide or direct another portion of the flow towards the first ends 22 of the cell channels 20.

Such flow guides 73 may be an efficient means of directing cells present in the biological sample towards to at least one identification surface 60, 61, to enable capture of selected cells by the affinity molecules.

Figure 8:
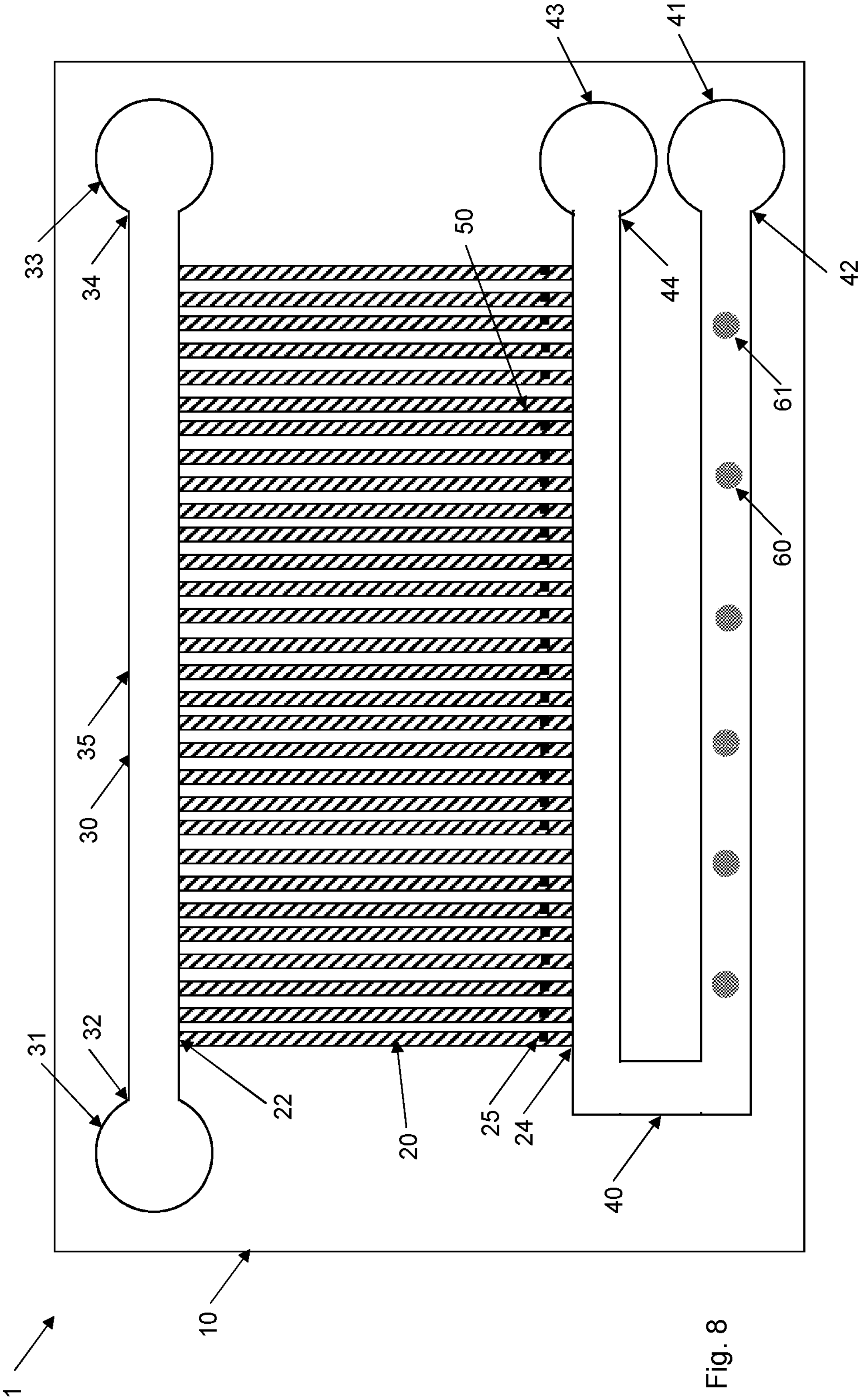
FIG. 8 is an illustration of a microfluidic device according to yet another embodiment.

FIG. 8 illustrates yet another embodiment of a microfluidic device 1. In this embodiment, the respective second end 24 of the spatially defined and separated cell channels 20 is in fluid connection with the flow output channel 40 in fluid connection with the third fluid port 41. In this embodiment, the at least one identification surface 60, 61 is at one surface of the flow output channel 40. Thus, in clear contrast to the embodiments shown in FIGS. 1-7, this embodiment of the microfluidic device 1 comprises the at least one identification surface 60, 61 in the flow output channel 40.

In a first embodiment, the flow output channel 40 is connected to a single fluid port 41 as shown in FIGS. 1-6. In such a case, cells can enter the flow output channel 40 and thereby become captured by the affinity molecules in the at least one identification surface 60, 61 according to different embodiments.

In a first embodiment, the biological sample is loaded into the third fluid port 41, which in this case operates as an input port, and is allowed to flow through the cell channels 20 towards the flow input channel 30 and out through the first fluid port 31 and/or the second fluid port 32. This reverse of the flow of biological sample can be performed prior to loading the biological material in the first fluid port 31 to allow cells present in the biological sample to enter the cell channels 20. Any excess cells not captured by the affinity molecules will then be flushed out through the third fluid port 41 when normal direction of the flow of the biological sample is established. Note that during the initial reverse flow direction of the biological sample most cells will not be able to enter cell channels 20 due to the obstructions 25 or only enter a small portion of the cell channels 20 between the obstructions 25 and the second ends 24.

In a second embodiment, no reversal of flow direction is performed. Instead the substrate 10 comprises reference channels 50. These reference channels 50 are basically cell channels lacking any obstruction 25. This means cells and other biological material present in the biological sample can enter the reference channels 50 from the flow input channel 30 and be transported into the flow output channel 40 to be captured by the affinity molecules or exit through the third flow port 41.

In another embodiment, the flow output channel 40 has a first end 42 in fluid connection with the third fluid port 41 and a second end 44 in fluid connection with a fifth fluid port 43. Accordingly, a flow of fluid can be established between the third and fifth fluid ports 41, 43. In such a case, the at least one identification surface 60, 61 can be provided at any surface portion of the flow output channel 40 between the first end 42 and the second end 44. For instance, the flow output channel 40 could be regarded as comprising a first intermediate channel portion and a second intermediate channel portion. In such a case, the respective second end 24 of the spatially defined and separated cell channels 20 is in fluid connection with the second intermediate channel portion. The first intermediate channel portion is provided between the first end 42 of the flow output channel 40 and the second intermediate channel portion and the second intermediate channel portion is provided between the first intermediate channel portion and the second end 44 of the flow output channel 40. The at least one identification surface 60, 61 could then be arranged in the first intermediate channel portion, in the second intermediate channel portion, at a position between the first intermediate channel portion and the second intermediate channel portion and/or between the second intermediate channel portion and the second end 44 of the flow output channel 40.

Figure 9:
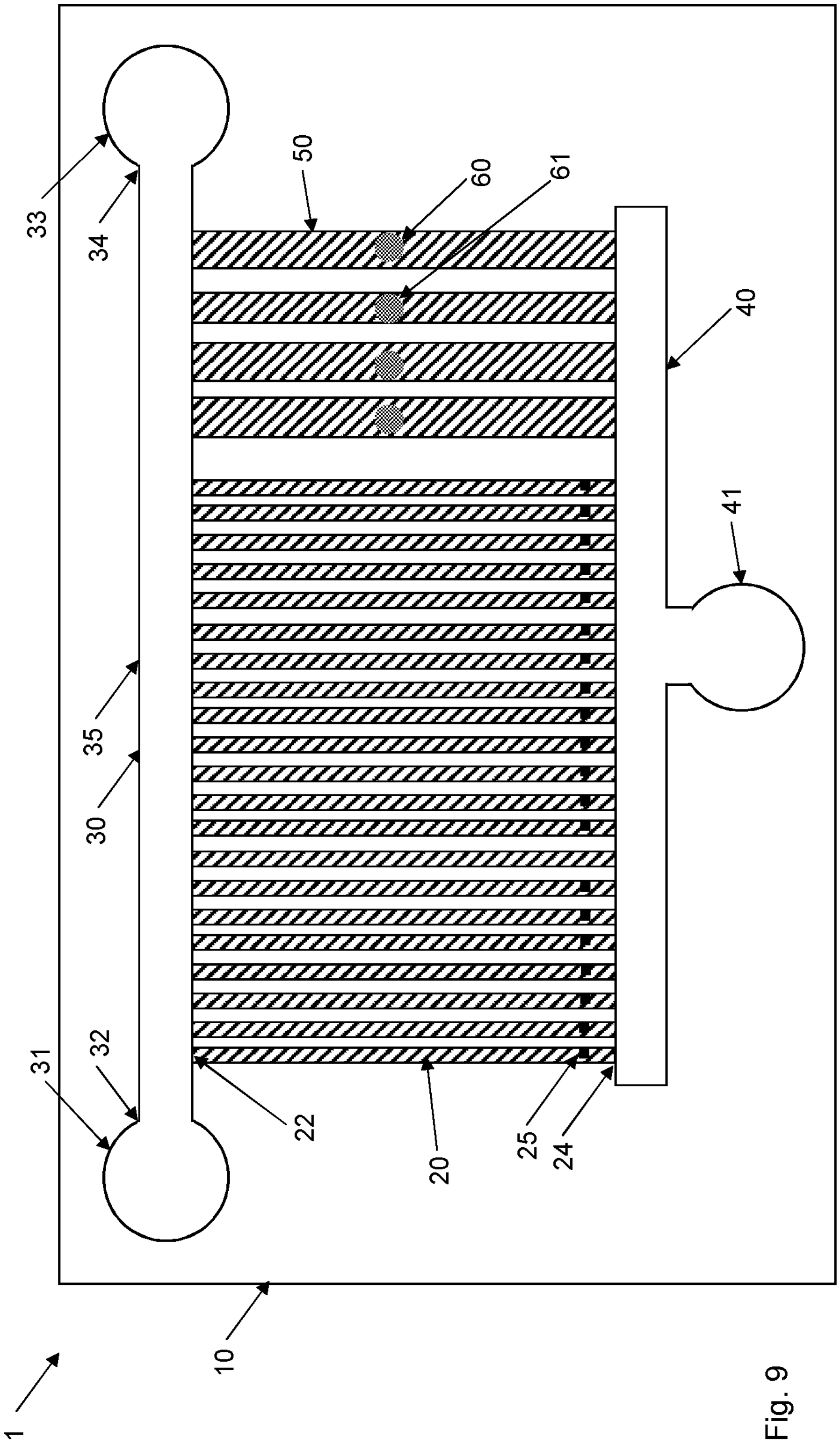
FIG. 9 is an illustration of a microfluidic device according to an embodiment.
Figure 10:
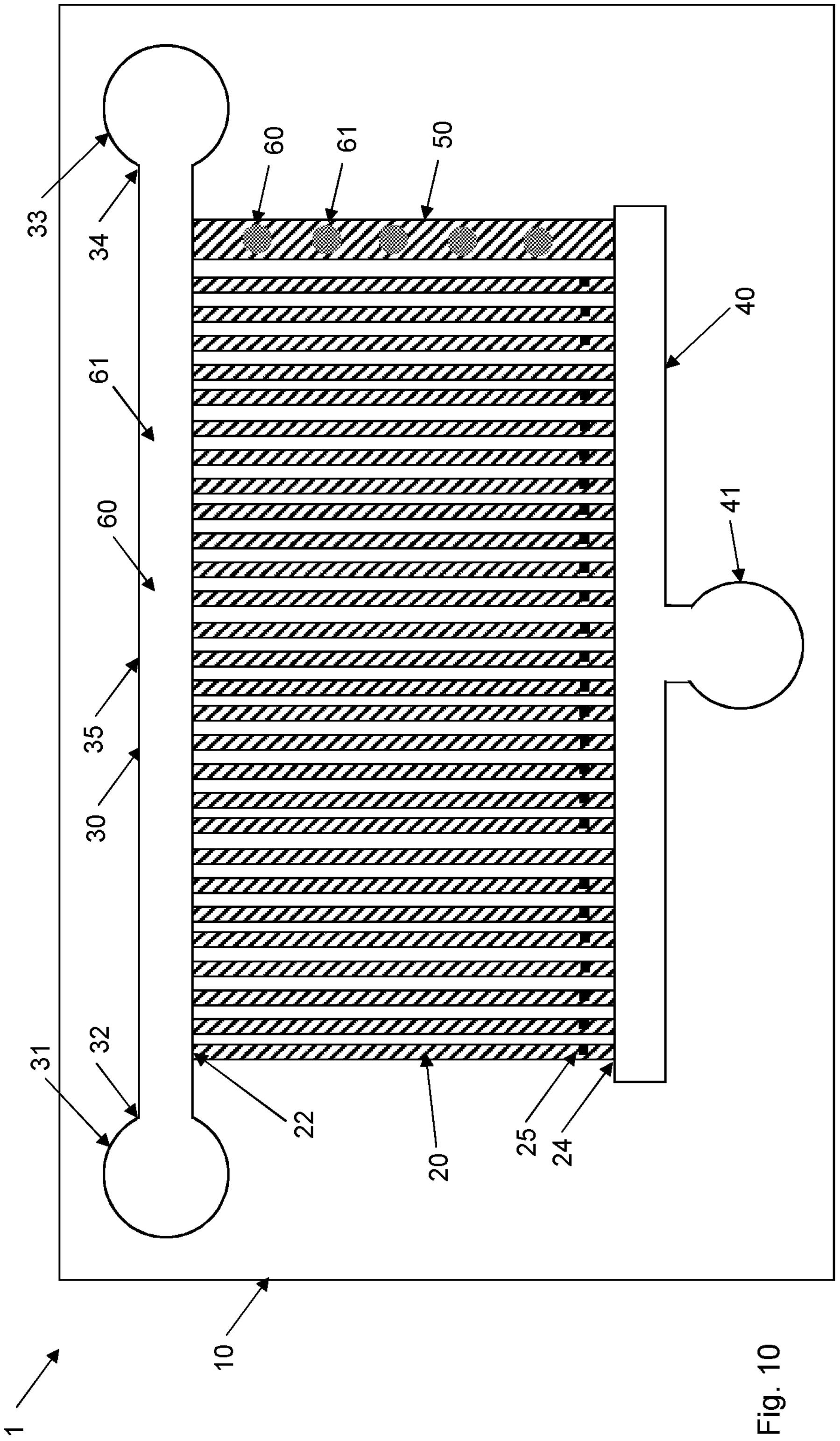
FIG. 10 is an illustration of a microfluidic device according to another embodiment.

FIGS. 9 and 10 illustrate a microfluidic device 1 according to further embodiments. In these embodiments, the substrate 10 of the microfluidic device 1 comprises at least one reference channel 50 having a first end in fluid connection with the flow input channel 30. The at least one identification surface 60, 61 is at least one surface of the at least one reference channel 50.

In an embodiment, the at least one reference channel 50 preferably has a second end in fluid connection with the flow output channel 40. Thus, the at least one reference channel 50 is preferably parallel with the spatially defined and separated cell channels 20.

The at least one reference channel 50 could be have the same dimensions, such as depth and width, and shape as the cell channels 20 but preferably lacks the obstruction 25 present in the cell channels 20. In an alternative embodiment, the at least one reference channel 50 could have different dimensions as compared to the cell channels 20, such as wider and/or deeper.

In an embodiment, the substrate 10 comprises multiple such reference channels 50 as shown in FIG. 9. In such a case, each such reference channel 50 or at least a portion thereof could comprise a respective identification surface 60, 61. In other embodiment as shown in FIG. 10, a reference channel 50 could comprise multiple identification surfaces 60, 61. It is of course possible to have multiple reference channels 50, of which all or at least a portion thereof, comprises multiple identification surfaces 60, 61.

Figure 11:
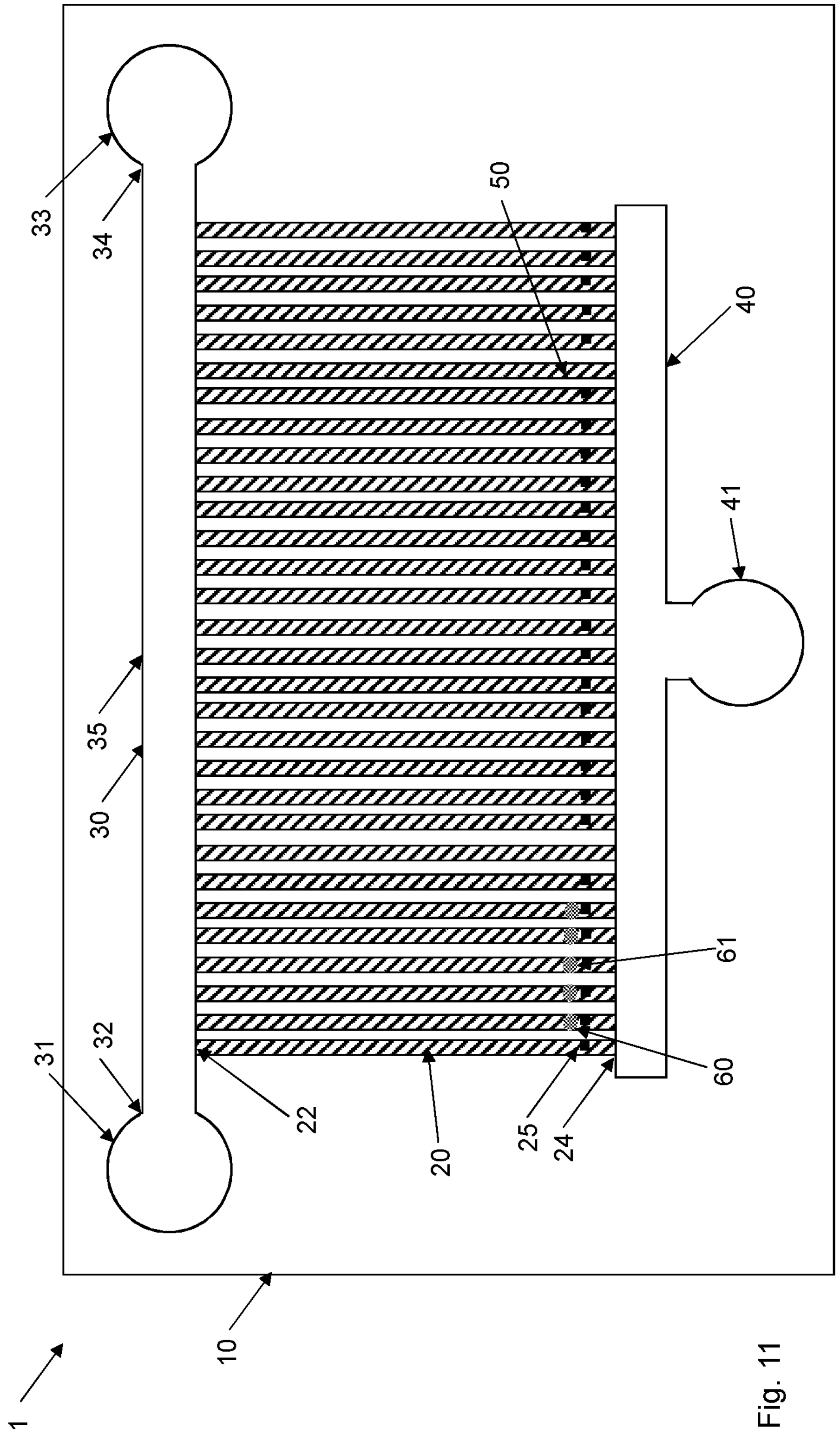
FIG. 11 is an illustration of a microfluidic device according to a further embodiment.

It is also, or alternatively, possible to have the at least one identification surface 60, 61 in one or more spatially defined and separated cell channels 20 as indicated in FIG. 11. This approach provides a comparatively long period of time for the cells to be captured by the affinity molecules in the at least one identification surface 60, 61. Non-captured cells can then be flushed away from the cell channels 20 by reversing the flow direction, i.e., use the third fluid port 41 as input fluid port and use the first and/or second fluid ports 31, 33 as output fluid ports. This have the additional advantage of providing an association between the identity of the cells, i.e., species, serotype or group thereof, and the phenotypic response of the cells. Thus, cells initially enter the cell channels 20 and are exposed to the target agent and the phenotypic response of the cells in the cell channels 20 is determined. Then, the flow direction is reversed to enable determination of whether any of the cells are captured by affinity molecules of identification surfaces 60, 61 present in the cell channels 20. This means that cells present in a given cell channel 20 can be assigned a species or serotype identity and a phenotypic response due to its presence in the given cell channel 20 and the capture of the cells by the at least one identification surface 60, 61.

Thus, in an embodiment, the at least one identification surface 60, 61 is at least one surface of at least one spatially defined and separated cell compartment 20.

In such an embodiment, each cell compartment, such as cell channel 20, could have one or more identification surfaces 60, 61 or a portion of the cell channels 20 comprise one or more identification surfaces 60, 61.

Figure 12:
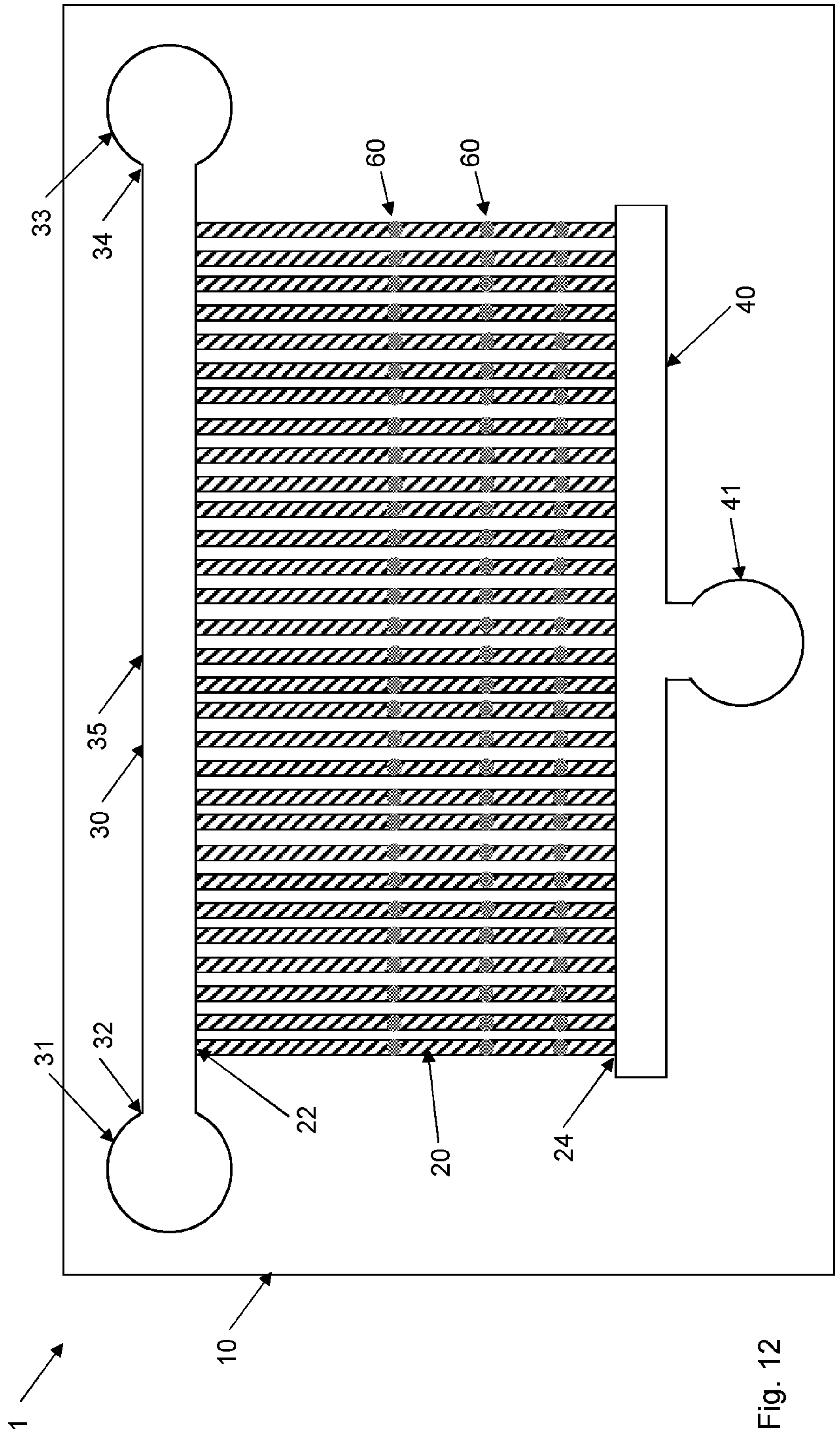
FIG. 12 is an illustration of a microfluidic device according to yet another embodiment.

FIG. 12 illustrates another embodiment of the microfluidic device 1 comprising identification surfaces 60, 61 arranged in the cell channels 20. In this embodiment, the cell channels 20 do not necessarily have any obstruction as previously disclosed herein. In clear contrast, capture of cells at an identification surface 60, 61 in a cell channel 20 preferably obstructs or blocks further cells from passing into the flow output channel 40. In this embodiment, the cell channels 20 advantageously have a width and height corresponding to or slightly larger than the diameter or width/height of the cells. Accordingly, once a cell has been captured by affinity molecules at an identification surface 60, 61, preferably no further cells can pass the captured cell in that cell channel 20. This means that physical obstructions in the cell channels 20 are not needed. In clear contrast, the selective capture of cells of a given species, serotype or group thereof takes the role of preventing cells from leaving the cell channels 20.

Figure 13:
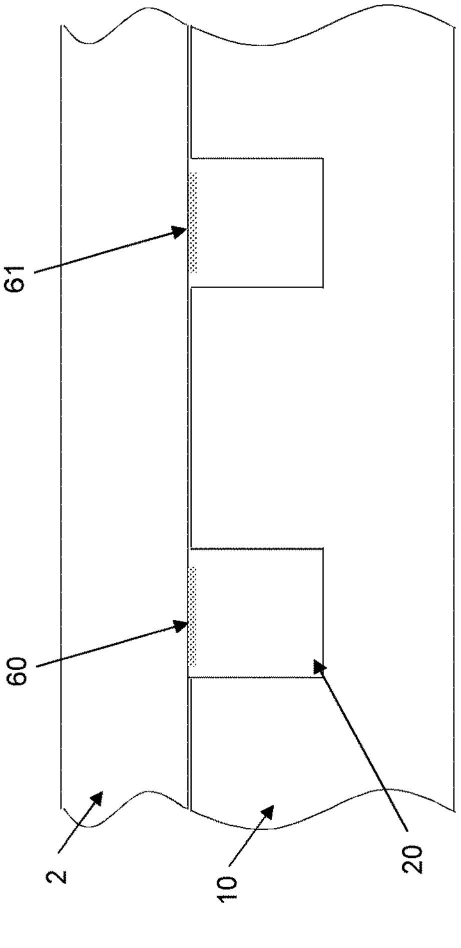
FIG. 13 is a cross-sectional view of a part of a microfluidic device according to an embodiment.

The embodiments described above have the at least one identification surface 60, 61 as a surface of the substrate 10. The present invention is, however, not limited thereto. In some embodiments the microfluidic device 1 comprises a substrate cover 2 attached to the substrate 10 as shown in FIG. 13. In such a case, the at least one identification surface 60, 61 is at least one surface of the substrate cover 2 aligned with at least one of the flow input channel, at least one cell channel 20 of the spatially defined and separated cell channels 20 and the flow output channel or indeed a reference channel.

The substrate cover 2 could be any cover that can be attached, preferably reversibly attached, to the substrate 10. Non-limiting, but illustrative, examples include cover slips or plates made of glass or plastics. In an embodiment, the substrate cover 2 is made of an optically transparent material, thereby enabling monitoring or detection of cells in the cell channels 20 and cells captured in identification surfaces 60, 61.

The at least one identification surface 60, 61 could then be at least one surface of the substrate cover 2. For instance, at least one surface of the substrate cover 2 aligned with flow input channel, or at least a portion thereof, when the substrate cover 2 is attached to the substrate 10, could constitute identification surface 60, 61 for the microfluidic device 1. Additionally, or alternatively, at least one surface of the substrate cover 2 aligned with the cell channels 20, or at least a portion of the cell channels 20, could be an identification surface 60, 61 and/or at least one surface of the substrate cover 2 aligned with the flow output channel, or at least a portion thereof.

In these embodiments, the affinity molecules of the at least one identification surface 60, 61 will extend into the flow input channel, cell channel(s) 20, and/or the flow output channel to thereby capture cells of a given species, serotype or group thereof, present in the flow input channel, cell channel(s) 20, and/or the flow output channel.

The various embodiments discussed in the foregoing and illustrated in FIGS. 1-13 may combined. Thus, the arrangement of identification surfaces 60, 61 in the various embodiments may be combined to provide such surfaces at multiple different positions in the flow input channel 30, in the flow output channel 40, in cell channel(s) 20, and/or in reference channel(s) 50 by arranging affinity molecules in the substrate 10 and/or in the substrate cover 2. Furthermore, the design of the flow input channel 30 in FIGS. 4-5 could be used in any of the embodiments shown in FIGS. 1-3, 6-13. Correspondingly, the flow output channel 40 according to FIG. 8 can be used in any other microfluidic devices in FIGS. 1-7, 9-13. A flow guide 73 as shown in FIG. 7 could be used in any of the microfluidic devices 1 in FIGS. 1-6, 8-13 Correspondingly, a channel branch 70 as shown in FIG. 6 could be provided elsewhere in the flow input channel and thereby be used in any of the embodiments 1-5, 7-13 and/or in the flow output channel 40 of FIG. 8.

In the foregoing, the reference channel(s) 50 have been described and illustrated as lacking any channel obstructions. In other embodiments, the reference channel(s) 50 may contain an obstruction similar to the cell channels 20. However, whereas the cell channels 20 have a respective obstruction 25 in connection with the second end 24, the reference channel(s) 50 then preferably has or have a respective obstruction in connection with a respective first end in fluid connection with the flow input channel 30. These embodiments are applicable in the case of preventing or at least restricting entry of cells present in a biological sample input through the first flow input 31 and flowing through the flow input channel 30 into the reference channel(s) 50. If the at least one identification surface 60, 61 is disposed in the reference channel(s) 50 then the reference channel(s) 50 preferably lack(s) any obstruction or the cells enter the reference channel(s) 50 through a reverse flow by inputting the biological sample through the third port 41 and the flow output channel 40.

Figure 14:
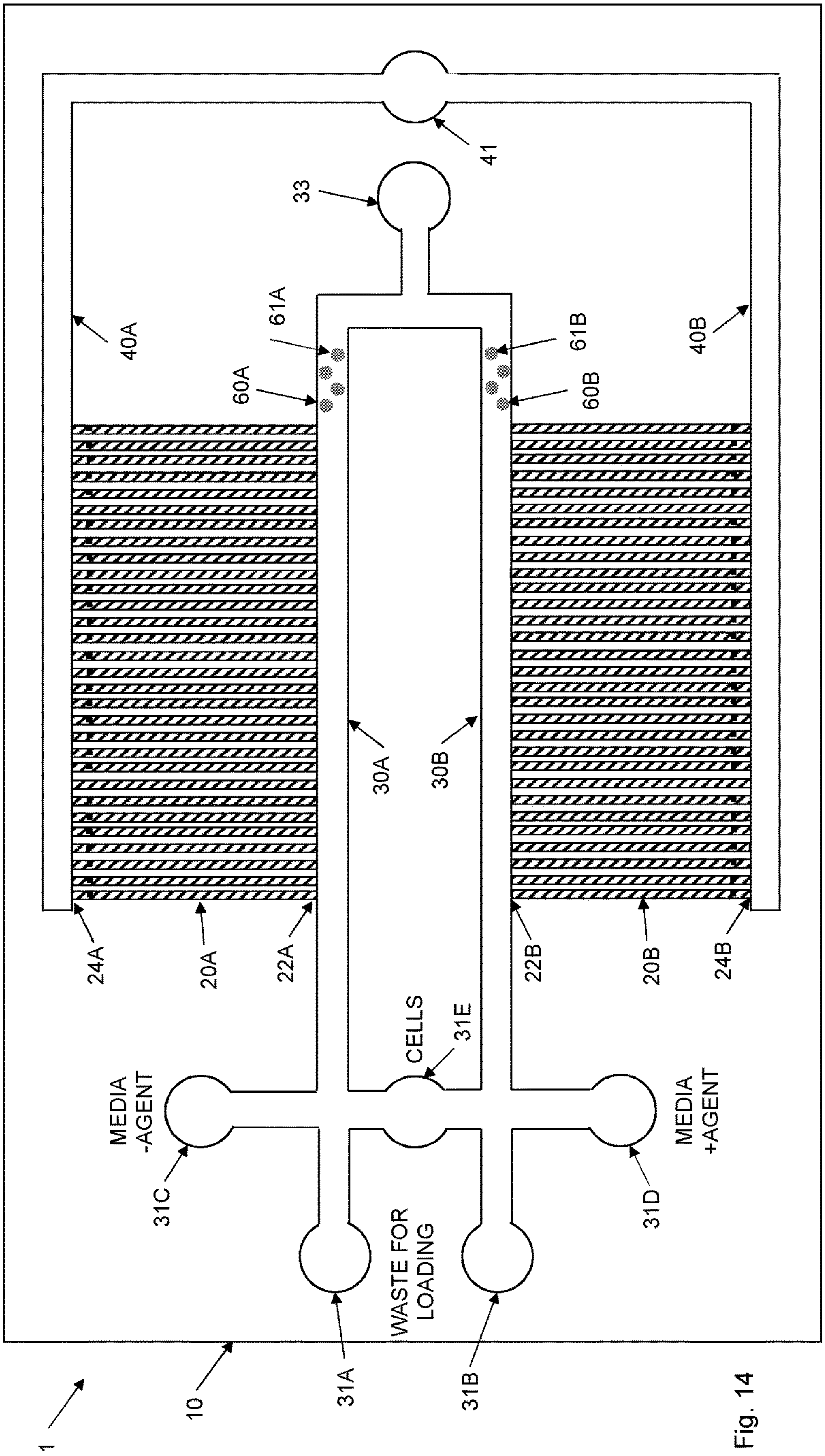
FIG. 14 is an illustration of a microfluidic device according to an embodiment.

The microfluidic devices 1 described above in connection with FIGS. 1-13 have been illustrated with reference to one set of spatially defined and separated cell channels 20. The embodiments are, however, not limited thereto. FIG. 14 illustrates an embodiment of a microfluidic device 1 comprising a substrate 10 having two sets of spatially defined and separated cell channels 20A, 20B. In this embodiment, a first flow input channel 30A is in fluid connection with a first fluid port 31A and second fluid port 33. A respective first end 22A of cell channels 20A in the first set is in fluid connection with this first flow input channel 30A. Correspondingly, a second flow input channel 30B is in fluid connection with a sixth fluid port 31B and the second fluid port 33. A respective first end 22B of cell channels 20B in the second set is in fluid connection with this second flow input channel 30B.

In the illustrated embodiment, the two flow input channels 30A, 30B have separate fluid ports 31A, 31B in one of their ends but a common fluid port 33 in the other ends. In alternative embodiments, each flow input channel 30A, 30B could have a separate fluid port in fluid connection with its respective ends or both flow input channels 30A, 30B could have common fluid ports in fluid connection with their respective ends.

The embodiment shown in FIG. 14 further illustrates the presence of additional fluid ports 31C-31D connected to the flow input channels 30A, 30B. In a particular embodiment, a common seventh fluid port 31E is used for loading cells or a biological sample into the microfluidic device 1. The first and sixth fluid ports 31A, 31B then operate as waste ports during loading, optionally together with the second port 33 and a third fluid port 41. An eighth fluid port 31C is in fluid connection with the first flow input channel 30A and thereby the cell channels 20A of the first set. Correspondingly, a ninth fluid port 31D is in fluid connection with the second flow input channel 30B and the cell channels 20B of the second set. These two fluid ports 31C, 31D can be used to expose cells present in the cell channels 20A, 20B to different media or solutions, such as a control medium or solution in the eighth fluid port 31C and a medium or solution with a test agent in the ninth fluid port 31D. This further means that any cells present in the cell channels 20A of the first set will be exposed to the control medium or solution, whereas any cells present in the cell channels 20B of the second set will be exposed to the medium or solution and the test agent.

The phenotypic response of cells to the test agent can thereby be determined and compared to control, i.e., phenotypic response of cells in the absence of the test agent, in a same microfluidic device 1 and at the same time.

The microfluidic device 1 preferably also comprises a first flow output channel 40A in fluid connection with the respective second end 24A of the cell channels 20A in the first set and a second flow output channel 40B in fluid connection with the respective second end 24B of the cell channels 20B in the second set. The two flow output channels 40A, 40B are, in the illustrated embodiment connected to a common third fluid port 41. In alternative embodiments, the flow output channels 40A, 40B could each be connected to a respective fluid port, have a respective fluid port connected to each of its ends, have a respective fluid port connected to one of its end and a common fluid port connected to the other of its end, or have common fluid ports connected to both its ends.

The at least one identification surface 60A, 60B, 61A, 61B could be arranged in the microfluidic device 1 according to any of the embodiments as disclosed herein. For instance, each flow input channel 30A, 30B could comprise respective at least one identification surface 60A, 60B, 61A, 61B.

The microfluidic device 1 could comprise more than two sets of spatially defined and separated cell channels 20A, 20B. This enables subjecting cells to various test agents, such as various culture media, in parallel in the same microfluidic device 1.

Figure 15:
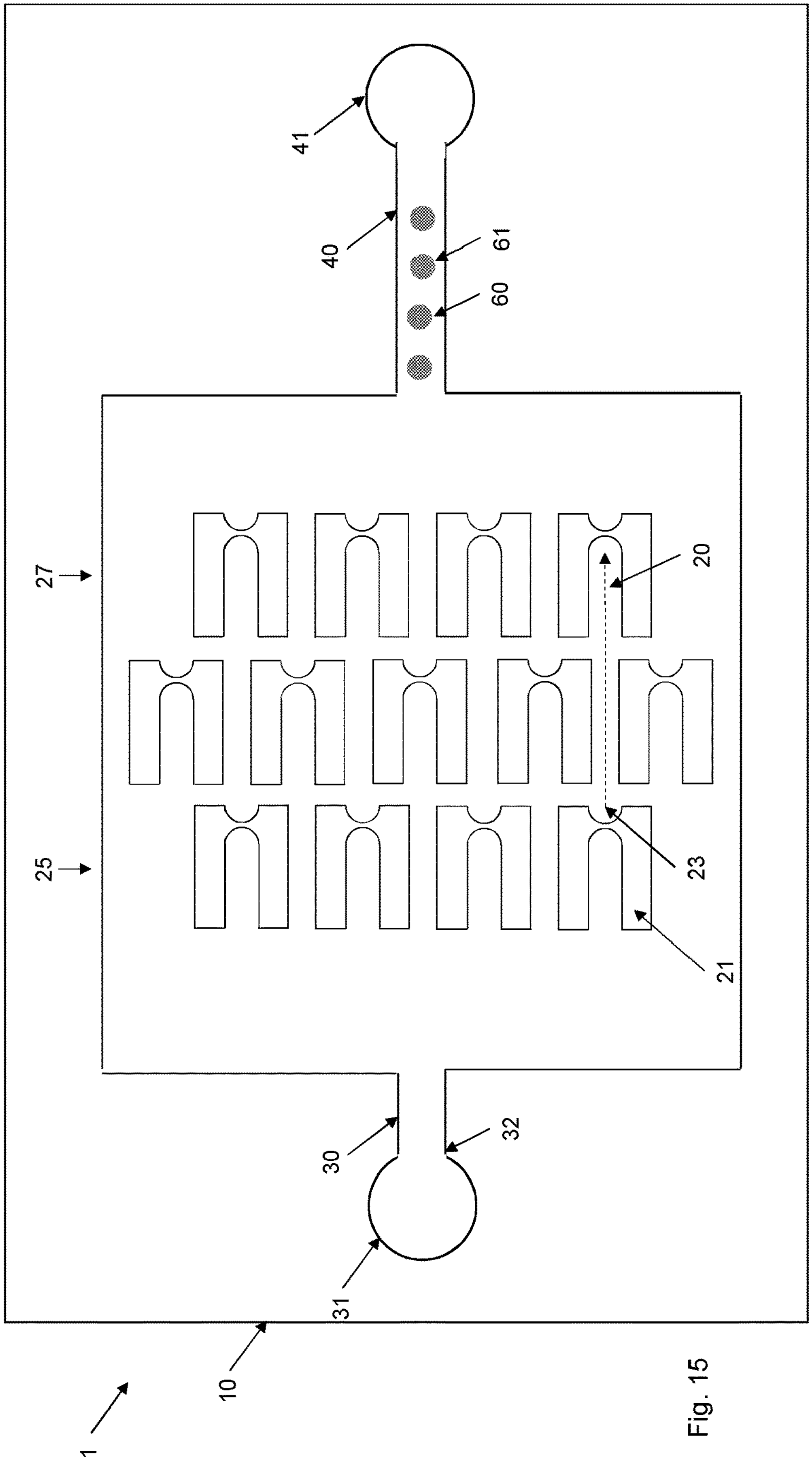
FIG. 15 is an illustration of a microfluidic device according to another embodiment.

The embodiments are not limited to the particular microfluidic devices described in the foregoing and illustrated in FIGS. 1-14. Also other microfluidic devices comprising spatially defined and separated cell compartments could be used according to the embodiments. An example of such another microfluidic device 1 is shown in FIG. 15.

The microfluidic device 1 comprises a substrate 10 having spatially defined and separated cell compartments in the form of cell traps 20 having a dimension, such as size and shape, to accommodate cells. The cell traps 20 are defined in a respective structure, denoted capture cups 21, to have a first end in fluid connection with a first flow channel 30 having an end 32 in fluid connection with a first fluid port 31. The substrate also comprises a second flow channel 40 in fluid connection with a second fluid port 41.

A biological sample is loaded into the second fluid port 41 to allow the biological sample to flow through the second flow channel 40, into a cell trap region and further into the first flow channel 30 and out from the first fluid port 31. Cells and non-cell material present in the biological sample will be captured in capture traps 23 forming the "backside" of the capture cups 21. When the flow is reversed, i.e., going from the first fluid port 31, into the first fluid channel 30, the cell trap region, and further into the second flow channel 40 and out from the second fluid port 41 cells and non-cell material captured in the capture traps 23 will be transferred in the direction of the flow into the larger cell traps 20 of a co-aligned and downstream arranged capture cup 21 as schematically illustrated by the hatched arrow in FIG. 15.

In an embodiment, the capture caps 21 comprises a thin channel between a cell trap 20 in a capture cap 21 and a capture trap 23 in the capture cap 21. This thin channel then facilitates a flow of culture medium out through the cell trap 20 and further into the aligned capture trap 23. This optional thin channel of the capture traps 23 is, however, too small to allow any cells from passing through the thin channel.

In an embodiment, the at least one identification surface 60, 61 is at least one surface of the second flow channel 40. In another embodiment, the at least one identification surface 60, 61 is at least one surface of the first flow channel 30. In a further embodiment, the at least one identification surface is at least one surface of the substrate 10 between the first flow channel 30 and the first column or row 25 of capture cups 21 and/or at least one surface of the substrate 10 between the second flow channel 40 and the last column or row 27 of capture cups 21.

As previously mentioned in the foregoing, the fluid ports of the microfluidic devices have been illustrated as being present in the substrates in FIGS. 1-15. This should merely be seen as an illustrative example. In an alternative embodiment, at least one of the fluid ports could be present outside of the substrate and then connected to the flow input channel(s) or flow output channel(s) with a respective tubing or other fluid connection.

The at least one identification surface in the substrate could have any suitable size and shape, including circular shape, elliptical shape, quadratic shape, rectangular shape, etc.

The microfluidic device may comprise a single identification surface comprising a single type of affinity molecules or a mixture of different types of affinity molecules. In another embodiment, the microfluidic device comprises multiple identification surfaces but these identification surfaces comprise the same single type of affinity molecules or the same mixture of different types of affinity molecules. In both these cases, the identification surface or surfaces and the affinity molecules immobilized thereon are configured to capture cells of given species or serotype or of a given group of species or serotypes.

A further alternative is to have multiple identification surfaces comprising different types of affinity molecules or different mixtures of affinity molecules. Hence, in such an embodiment the microfluidic device comprises multiple identification surfaces. The affinity molecules immobilized onto an identification surface of the multiple identification surfaces are configured to capture cells of a first species or serotype or of a first group of species or serotypes. The affinity molecules immobilized onto other identification surface or surfaces of the multiple identification surfaces are configured to capture cells of a second, different species or serotype or of a second, different group of species or serotypes.

In this embodiment, the microfluidic device can be used to identify different species, serotypes or groups thereof present in a biological sample by having multiple identification surfaces configured to capture different such cell species, serotypes or groups thereof.

The affinity molecules immobilized onto the identification surface or surfaces in the microfluidic device could have affinity for at least one cell surface molecule, or structure, specific for the cells of the species or serotype or the group thereof. The cell surface molecules could be molecules present in the cell membrane, molecules in the cell wall, molecules in flagella, molecules in fimbriae, and/or molecules in the glycocalyx.

In the above presented examples, the affinity molecules bind directly to extracellular molecules expressed by cells. The embodiments are, however, not limited thereto. In other embodiments, the affinity molecules are secondary affinity molecules having affinity for primary affinity molecules. The primary affinity molecules then have affinity for at least one cell surface molecule expressed by cells of the species or serotype or the group thereof.

Hence, in these embodiments so-called primary affinity molecules have affinity for cell surface molecules made by at least some of the cells in a biological sample, and optionally as exemplified above. The affinity molecules immobilized onto the at least one identification surface then have affinity for and thereby capability to bind to the primary affinity molecules. Accordingly, the cells expressing the cell surface molecules will be captured at an identification surface through the binding between the primary affinity molecules and the cell surface molecules and the binding between the immobilized secondary affinity molecules and the primary affinity molecules. In such a case, the primary affinity molecules can be added to the biological sample prior to loading into the microfluidic device, in connection with loading into the microfluidic device or indeed following loading of the biological sample, such as using a different fluid port as compared to the sample loading port.

It is of course possible to combine the above described embodiments with regard to affinity molecules. For instance, at least one identification surface may comprise immobilized affinity molecules having affinity for at least one cell surface molecule, whereas at least one other identification surface may comprise immobilized secondary affinity molecules having affinity for primary affinity molecules. In fact, it is possible to mix both secondary affinity molecules and affinity molecules having affinity for at least one cell surface molecule in the same identification surface.

In an embodiment, the affinity molecules immobilized onto the at least one identification surface are antibodies, or fragments thereof.

According to the embodiments, the antibody could be a monoclonal antibody or a polyclonal antibody.

In an embodiment, the affinity molecule is a fragment of an antibody. Non-limiting, but illustrative, examples of such antibody fragments can be selected from the group consisting of a single chain antibody, a Fv fragment, a scFv fragment, a Fab fragment, a F(ab')2 fragment, a Fab' fragment, a Fd fragment, a single-domain antibody (sdAb), a scFv-Fc fragment, a di-scFv fragment and a complementarity-determining region (CDR) region.

The specificity of an antibody, or indeed any affinity molecule, can be determined based on affinity and/or avidity. The affinity, represented by the equilibrium constant for the dissociation of an antigen with the antibody ($K_d$), is a measure for the binding strength between an antigenic determinant and an antigen-binding site on the antibody. The lesser the value of $K_d$, the stronger the binding strength between the antigenic determinant and the antibody. Alternatively, the affinity can also be expressed as the affinity constant ($K_a$), which is $1/K_d$. As will be clear to the skilled person, affinity can be determined in a manner known per se, depending on the specific antigen of interest.

Avidity is the measure of the strength of binding between an antibody and the pertinent antigen. Avidity is related to both the affinity between an antigenic determinant and its antigen binding site on the antibody and the number of pertinent binding sites present on the antibody.

Typically, antibodies will bind to their antigen with a dissociation constant ($K_d$) of $10^{-5}$ to $10^{-12}$ moles/liter (M) or less, and preferably $10^{-7}$ to $10^{-12}$ M or less and more preferably $10^{-8}$ to $10^{-12}$ M, i.e. with an association constant ($K_a$) of $10^5$ to $10^{12}$ $M^{-1}$ or more, and preferably $10^7$ to $10^{12}$ $M^{-1}$ or more and more preferably $10^8$ to $10^{12}$ $M^{-1}$.

Generally, any $K_d$ value greater than $10^{-4}$ M (or any $K_a$ value lower than $10^4$ $M^{-1}$) is generally considered to indicate non-specific binding.

Specific binding of an antibody to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art.

Antibodies and fragments thereof are preferred examples of affinity molecules that can be immobilized onto the at least one identification surface. However, also other types of affinity molecules can be used according to the embodiments. For instance, receptor ligands could be used as affinity molecules in order to capture cells expressing the corresponding receptor on the cell surface.

Other types of affinity molecules that can be used for this purpose include, for example, designed ankyrin repeat proteins (DARPin), aptamers, affibodies, bacteriophages, adhirons, and nanobodies.

The affinity molecules can be immobilized onto the at least one identification surface according to various embodiments depending on, for instance, the material of the substrate, the substrate cover and/or the type of affinity molecules. For instance, the surface of a silicon substrate could be subject to silanization to activate at least the surface portion(s) of the substrate corresponding to the at least one identification surface. Affinity molecules, such as antibodies, can then be covalently linked to the activated surface of the substrate.

In an example, a pre-cleaned silicon substrate is soaked in a solution of (3-aminopropyl)triethoxysilane (APTES) in methanol, such as 2% and for 15 min, followed by further incubation in a solution of N-β-maleimidopropyl-oxysuccinimide ester (BMPS) in anhydrous acetonitrile, such as 10 mM and for 30 min. Antibody solution can then be deposited onto the activated substrate surface as small droplets and incubated in room temperature, such as for 1 hour, to allow covalent linking of the antibodies to the substrate surface.

Also other methods of immobilizing affinity molecules to the substrate and/or substrate cover can be used according to the embodiments. For instance, streptavidin, or avidin, and biotin could be used to immobilize the affinity molecules onto the substrate and/or substrate cover. In such a case, streptavidin or avidin may be attached to the substrate and/or substrate cover and each affinity molecule is then tagged with a biotin tag to immobilize the affinity molecules onto the substrate and/or substrate cover through the streptavidin/avidin—biotin linkage. It is of course possible to attach avidin onto the substrate and/or substrate cover and then tag the affinity molecules with streptavidin or avidin tags.

Also the hybridization of complementary nucleotide sequences, such as DNA or RNA sequences, could be utilized to immobilize the affinity molecules. In such a case, nucleotide sequences are attached to the substrate and/or substrate cover using techniques well known in the art. The affinity molecules are then tagged with a nucleotide sequence complementary to and capable of base pairing with at least one nucleotide sequence attached to the substrate. The formation of a double stranded nucleotide sequence following hybridization efficiently anchors the affinity molecules onto the at least one identification surface. This approach has the additional advantage of controlling which affinity molecules that should be attached onto which identification surface(s) by using different nucleotide sequences and different complementary nucleotide sequences.

The affinity molecules could be directly immobilized onto the substrate and/or substrate cover at the at least one identification surface, such as covalently linked to the substrate and/or substrate cover. It is, however, possible to use a linker, spacer or connector in between the substrate and/or substrate cover and the affinity molecules. In such a case, such a linker, spacer or connector is attached, such as covalently linked, to the substrate (cover) surface and attached to at least one affinity molecule to thereby immobilize the at least one affinity molecule onto the at least one identification surface.

The substrate of the microfluidic device may be made of any suitable material, such as plastic material, in which the structures constituting the spatially defined and separated cell compartments, flow channels and identification surfaces can be defined. Non-limiting examples of suitable materials include ZEONEX® and ZEONOR®, which are cyclic olefin polymers (COP) marketed by ZEON Chemicals L.P. and TOPAS®, which are cyclic olefin copolymers (COC) marketed by Topas Advanced Polymers. These materials have excellent optical characteristics in terms of transmission and background fluorescence. They also have good flow characteristics when heated and may therefore replicate small structures allowing formation of substrates of the microfluidic device.

Other examples of suitable materials for the substrate include glasses, polydimethylsiloxane (PDMS), poly (methyl methacrylate) (PMMA), polycarbonate (PC), polypropylene (PP), polytetrafluoroethylene (PTFE), polyethylene terephthalate (PET) and poly(p-phenylene sulfide) (PPS).

Figure 16:
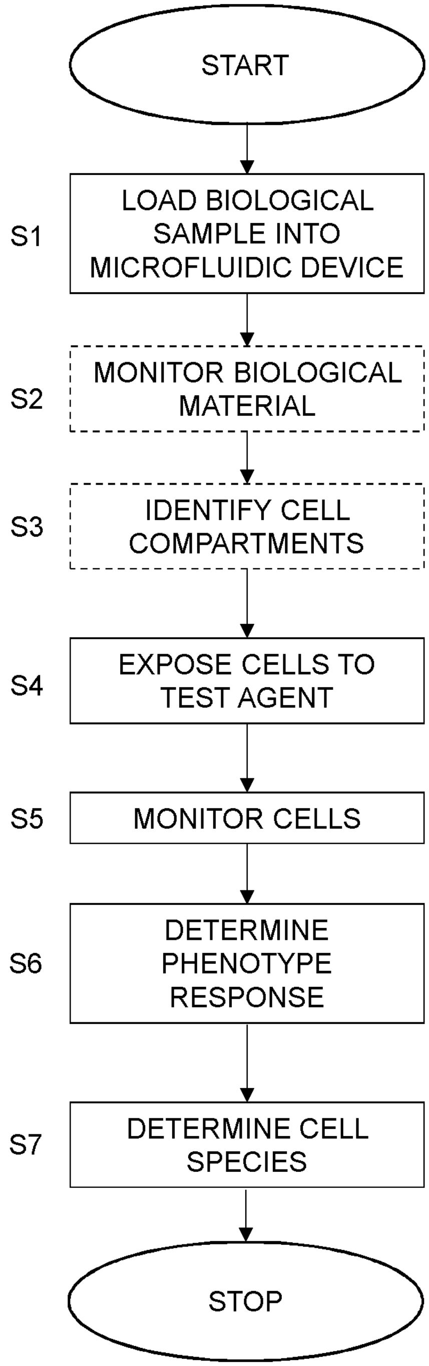
FIG. 16 is a flow chart illustrating a method of characterizing cells according to an embodiment.

FIG. 16 is a flow chart illustrating a method of characterizing cells according to an embodiment. The method comprises loading, in step S1, a biological sample comprising cells into a microfluidic device according to the embodiments to capture cells in the spatially defined and separated cell compartments. The method also comprises exposing, in step S4, cells in the spatially defined and separated cell compartments to a test agent and monitoring, in step S5, cells in the spatially defined and separated cell compartments. The method further comprises determining, in step S6, a phenotypic response of cells to the test agent based on monitoring the cells in the spatially defined and separated cell compartments. The method additionally comprises determining, in step S7, a species or serotype or a group of species or serotypes based on presence of cells captured by the affinity molecules immobilized onto the at least one identification surface.

In FIG. 16, step S7 has been illustrated following step S6. However, the determining the species, serotype or group thereof can be performed any time following step S1, i.e., prior to or following any of steps S2-S6 or indeed at least partly in parallel with any of steps S2-S6.

The characterization of cells according to the embodiments thereby not only determine the phenotypic response of cells to a target agent but also provides an identification of cells in terms of determining the species or serotype of the cells, or determining a group of species or serotypes to which the cells belong. This means that a more complete characterization of cells in the biological sample is obtained as compared to merely trying to identify the species or serotype or only determining cell response to a test agent, which will be described in more detail herein.

In some cases, there may be problems and difficulties in characterizing cells in a biological sample in a microfluidic device due to the heterogeneity of the biological sample and the presence of several types of cells and non-cell material that may negatively affect the characterization.

For instance, characterizing target cells may be performed by monitoring the response of cells to a stimuli, such as exposure to a test agent, a particular environmental condition, etc. If the cells constitute a minority of the material that is captured and monitored in the microfluidic device the phenotyping may be flawed by the presence of other cells and non-cell material. In the worst case, the phenotypic characterization of the relevant cells may be incorrect thereby assigning an incorrect phenotype to the cells.

A typical example is testing antibiotic susceptibility of bacteria present in urine from a patient suffering from urinary tract infection (UTI). If the urine sample is contaminated by cells and bacteria from, for instance, the skin, such contaminating cells may constitute the vast majority of the cells in the urine sample loaded into the microfluidic device. The contaminating bacteria will, however, most likely not grow or survive in the urine sample due to the constituents and pH of the urine sample. If the cells loaded in the microfluidic device are exposed to an antibiotic to test the susceptibility of the UTI-causing bacteria in the urine then most of the captured cells will not grow, not mainly because the presence of the antibiotic but due to the contaminating cells will not grow in urine or other selective media. Monitoring the growth of cells in the microfluidic device in the presence of antibiotic may therefore conclude that UTI-causing bacteria are susceptible to the antibiotic since most of the cells captured in the microfluidic device do not grow in the presence of antibiotic. This means that the growth of insusceptible or resistant bacteria in the urine may be overshadowed by the non-growth of the cells that are not viable in urine. As a result, the UTI-causing bacteria in the urine may be incorrectly classified as susceptible to the antibiotic even if they really are resistant to the antibiotic. This may in turn have grave consequences when treating a patient from whom the urine sample was taken by administering an antibiotic that will not significantly inhibit growth of the insusceptible bacteria present in the patient's urine.

The combined phenotyping and species/serotype determination of the embodiments solves the above problem with heterogeneity by not only monitoring phenotypic response but also identifying cell species or serotype. This combination thereby provides a more accurate characterization of the cells and enable determining the correct phenotypic response of target cells by further identifying the presence of these target cells in the biological sample at the identification surface(s).

For instance, in such embodiments with mixed populations of cells it may be advantageous to determine the phenotypic response also based on information of the determined species, serotype or group thereof. In such a case, the determined phenotypic response can be stratified in the analysis based on the species or serotype information. This in turns enables assigning different determined phenotypic responses to different cells species, serotypes or groups thereof by also having access to the species or serotype information.

In some embodiments, information of a phenotypic response of cells to a test agent, such as a selective medium that only sustains growth of one or more cell species, may facilitate in determining the species or serotype of the cells. Hence, in such an embodiment, step S7 of FIG. 16 comprises determining the species or serotype or the group of species or serotypes based on presence of cells captured by the affinity molecules immobilized onto the at least one identification surface and based on the determined phenotypic response.

In a particular embodiment, step S1 of FIG. 16 comprises loading a biological sample comprising biological material including cells into a microfluidic device according to the embodiments. In this particular embodiment, the method further comprises monitoring, in step S2, biological material in the spatially defined and separated cell compartments. A subset of the spatially defined and separated cell compartments is identified in step S3 as comprising cells exhibiting at least one phenotypic characteristic as determined based on the monitoring of biological material in the spatially defined and separated cell compartments.

In this particular embodiment, step S4 comprises exposing biological material in the spatially defined and separated cell compartments to a test agent. A following step S5 comprises, in this particular embodiment, monitoring cells in the identified subset of the spatially defined and separated cell compartments. A phenotypic response of the cells to the test agent is then determined in step S6 based on the monitoring of cells in the identified subset of the spatially defined and separated cell compartments.

The method of this particular embodiment thereby involves a selection step to identify those spatially defined and separated cell compartments of the microfluidic device that comprise so-called "target cells" prior to determining the phenotypic response of the target cells. Thus, biological material captured or loaded in the spatially defined and separated cell compartments is monitored to identify the spatially defined and separated cell compartments that comprise biological material exhibiting the at least one target phenotype characteristic. The phenotypic response is then determined in step S6 based only on the response of the biological material, i.e., target cells, that is present in the spatially defined and separated cell compartments identified in step S3. Accordingly, biological material in the remaining spatially defined and separated cell compartments is cells and non-cell material other than the target cells as determined based on not exhibiting the at least one target phenotype. The responses of such material in the remaining spatially defined and separated cell compartments are thereby disregarded and not used when determining the phenotypic response in step S6.

This mean that the phenotypic response as determined in step S6 is in fact the true response of the target cells to the test agent in the biological material and this phenotypic response will not be overshadowed or affected by the responses of other cells and non-cell material in the biological sample.

For instance, assume that the biological sample is a urine sample taken from a patient suffering from UTI and that the susceptibility of UTI-causing bacteria as target cells to an antibiotic is to be tested in the method shown in FIG. 16. The urine sample is then loaded in step S1 into the microfluidic device to capture the UTI-causing bacteria and any contaminating bacteria and cells in the spatially defined and separated cell compartments. The contaminating bacteria and cells are typically not viable in the urine and will thereby not grow or at least grow slowly. Accordingly, step S2 may, for instance, involve monitoring the biological material in the spatially defined and separated cell compartments with the purpose of determining their viability or cell growth. Step S3 may therefore involve identifying the subset or portion of the spatially defined and separated cell compartments that comprise cells that are viable and/or have a growth rate exceeding a target growth rate as determined based on the monitoring in step S2. The biological material in this identified subset is thereby viable and growths well in the urine and thereby mainly constitute of the UTI-causing bacteria. Material in the remaining spatially defined and separated cell compartments is not viable and has a growth rate below the target growth rate. This material thereby mainly consists of contaminating cells and bacteria and non-cell material from the urine sample.

The biological material in the spatially defined and separated cell compartments is then exposed to the antibiotic and the biological material, i.e., UTI-causing bacteria, present in the spatially defined and separated cell compartments identified in step S3 is monitored in step S5 and the phenotypic response of this biological material, i.e., UTI-causing bacteria, to the antibiotic is then determined in step S6 based on the monitoring in step S5. The susceptibility or resistance of the UTI-causing bacteria to the antibiotic can thereby efficiently be determined in step S6 without the risk of overshadowing or influence from the response of the contaminating cells or bacteria from the urine sample.

The method additionally determines the species, serotype or group thereof in step S7 to achieve a full characterization of the UTI-causing bacteria.

In an embodiment, the substrate comprises a first set of spatially defined and separated cell compartments having a dimension to accommodate cells and a second set of spatially defined and separated cell compartments, such as shown in FIG. 14. In such an embodiment, step S4 could comprise exposing cells in the second set of spatially defined and separated cell compartments to a solution comprising the test agent and exposing cells in the first set of spatially defined and separated cell compartments to the solution lacking the test agent. Step S5 then preferably comprises monitoring cells in the first set of spatially defined and separated cell compartments and cells in the second set of spatially defined and separated cell compartments. In this embodiment, step S6 comprises determining a phenotypic response of cells to the test agent based on monitoring the cells in the first set of spatially defined and separated cell compartments and cells in the second set of spatially defined and separated cell compartments.

This embodiment thereby has a parallel control in terms of the cells present in the spatially defined and separated cell compartments of the first set. This means that in an embodiment, the phenotypic response of cells to the test agent is determined based on a comparison of the cells in the first set of spatially defined and separated cell compartments and the cells in the second set of spatially defined and separated cell compartments.

In an embodiment, the test agent is an antibiotic. In such a case, step S5 preferably comprises measuring first relative time-dependent changes in occupation of cells in the spatially defined and separated cell compartments without exposure to the antibiotic and measuring second relative time-dependent changes in occupation of cells in the spatially defined and separated cell compartments with exposure to the antibiotic.

In a first case, this embodiment of step S5 is performed serially, i.e., first monitoring cells in the spatially defined and separated cell compartments without any addition of the antibiotic to measure the first relative time-dependent changes in cell occupation. Then the antibiotic is added and the cells are anew monitored in the spatially defined and separated cell compartments to measure the second relative time-dependent changes in cell occupation. In this first case, the monitored cells are their own control.

In a second case, this embodiment of step S6 is performed in a parallel as mentioned above, such as using a microfluidic device as shown in FIG. 14 comprising at least two sets of spatially defined and separated cell compartments.

In this embodiment, step S6 preferably comprises determining an antibiotic susceptibility of cells based on the first relative time-dependent changes and the second relative time-dependent changes and based on information of the species or serotype or said group of species or serotypes.

In particular, the susceptibility of the cells to the antibiotic is preferably determined based on a comparison of the first and second relative time-dependent changes and based on the species or serotype information.

The inclusion of species or serotype information in the determination of antibiotic susceptibility is an advantage especially with a biological sample comprising a mixed population of cells species or serotypes. In such a case, the relative time-dependent changes in cell occupation can be stratified in the analysis by means of the species or serotype information.

Furthermore, in an embodiment, the method comprises an additional step of determining an antibiotic susceptibility of cells based on the determined phenotypic response and based on the determined species or serotype or said group of species or serotypes.

In an embodiment, the microfluidic device comprises multiple identification surfaces. In this embodiment, affinity molecules immobilized onto an identification surface of the multiple identification surfaces are configured to capture cells of a first species or serotype or of a first group of species or serotypes and affinity molecules immobilized onto other identification surface(s) of the multiple identification surfaces are configured to capture cells of a second, different species or serotype or of a second, different group of species or serotypes. Each identification surface of the multiple identification surfaces is associated with a respective species or serotype or a respective group of species or serotypes. In such a case, step S7 of FIG. 16 preferably comprises determining a respective species or serotype or a respective group of species or serotypes based on presence of cells captured by the affinity molecules immobilized onto the multiple identification surfaces.

Thus, in this embodiment, different identification surfaces have different affinity molecules or different mixture of affinity molecules to thereby capture cells of different species, serotypes or groups thereof. For instance, a first identification surface comprises affinity molecules for capturing a first serotype of a cell species, a second identification surface comprises affinity molecules for capturing a second serotype of the cell species, and so on. In such a case, serotypes of cells present in the biological sample can be identified based on which identification surface(s) that comprise(s) captured cells.

The microfluidic device as shown in FIG. 7 had a flow guide to guide the flow towards the identification surface(s). In an alternative, or additional, approach a field can be applied to at least a portion of the microfluidic device to direct cells towards the at least one identification surface. Such a field could then be an electric field, a magnetic field, an acoustic field or a combination thereof. For instance, surface charges of cells can be used to guide the cells towards the at least one identification surface. Correspondingly, an acoustic field could provide pressure waves forcing the cells towards the at least one identification surface. Magnetic fields can be used to guide magnetic labelled cells towards the at least one identification surface.

This approach could be regarded as a form of field flow fractionation, such as dielectrophoresis, acoustophoresis or magnetophoresis, to guide objects, such as cells, based on various properties, such as electric properties, size properties or magnetic properties.

In an embodiment, the biological sample is a body fluid sample, such as a urine sample, a blood sample, a saliva sample, a feces sample, a cerebrospinal fluid sample, an amniotic fluid sample, a milk sample, or a lymph sample. Alternatively, the biological sample could be obtained from a body tissue, such as a biopsy. Other examples include food sample tested for bacterial contaminations, milk from cow, goats or other milk producing animals for mastitis testing, etc. Actually, any biological sample that comprises cell and that can be loaded into a microfluidic device can be used according to the embodiments.

Cells could be bacteria, e.g., *Escherichia, Klebsiella, Staphylococcus* cells, archaea cells, eukaryotic cells, yeast cells, animal cells, human cells, cancer cells, etc., present in a biological sample. These cells should be characterized in the method of the embodiments.

This test agent could be any molecule, compound, composition, or a mixture of molecules, compounds or compositions, or a selective growth medium. In related embodiments, the biological material is more generally exposed to a stimuli in the spatially defined and separated cell compartments. Such a stimuli does not necessarily have to be a test agent but could instead be a change in environmental conditions, such as temperature change.

Illustrative, but non-limiting, examples of target phenotype characteristics determined in step S3 of FIG. 16 but also phenotypic response determined in step S6 could be growth rate, shape, size, shape of growth rate curve defining growth rate overtime, form of length curve defining cell length overtime, shape of area curve defining cell area over time, color, optical density, absorption spectra, and a mixture of at least two such phenotype characteristics.

A target phenotype characteristic can be the complement of a characteristic of the non-target cell material. Thus, target phenotype characteristic could be the lack of a given phenotypic characteristic. In such a case, non-target cell material exhibit the phenotypic characteristic, whereas the target cells have the target phenotype characteristic by not exhibiting the given phenotypic characteristic.

Figure 20A:
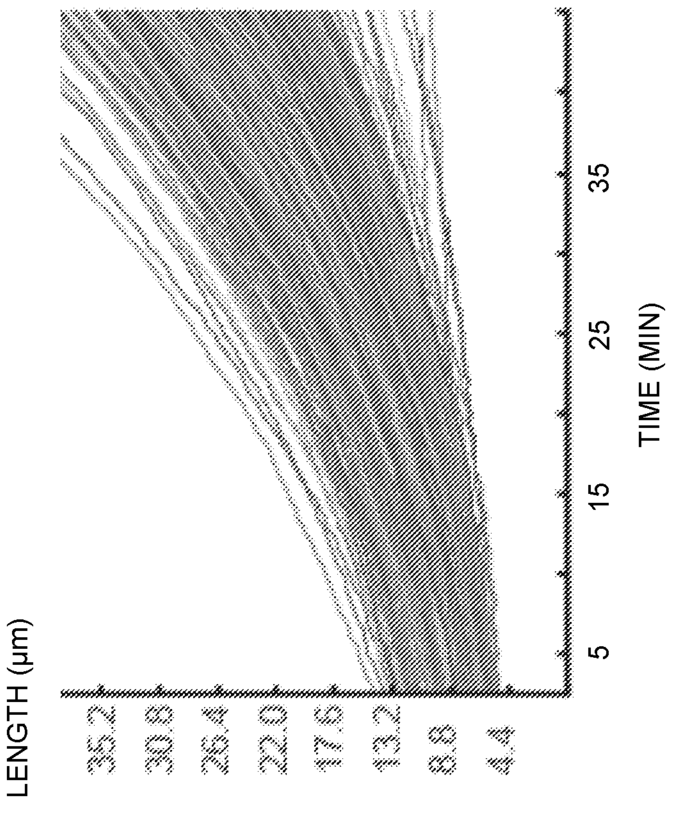
FIGS. 20A and 20B show length (FIG. 20A) and growth rate (FIG. 20B) as a function of time plotted for individual cell channels of a microfluidic device.

Growth rate in a given culturing condition, such as selected culture medium, is a phenotypic characteristic or trait that can advantageously be used to discriminate target cells from other material. Growth rate can be determined, for instance, by monitoring the number of cells or particles or their position in each spatially defined and separated cell compartment as the number will increase over time for growing cells. Alternatively, or in addition, grow rate can be determined by monitoring the length of the portion of a spatially defined and separated cell compartment occupied by cells or particles. This length will increase over time for growing cells but remain the same for non-viable and non-growing cells and non-cell material. FIG. 20A illustrate such length over time in spatially defined and separated cell compartments of a microfluidic device. Alternatively, or in addition, grow rate can be determined by monitoring the area or length of cells segmented in images of the spatially defined and separated cell compartments.

Figure 20B:
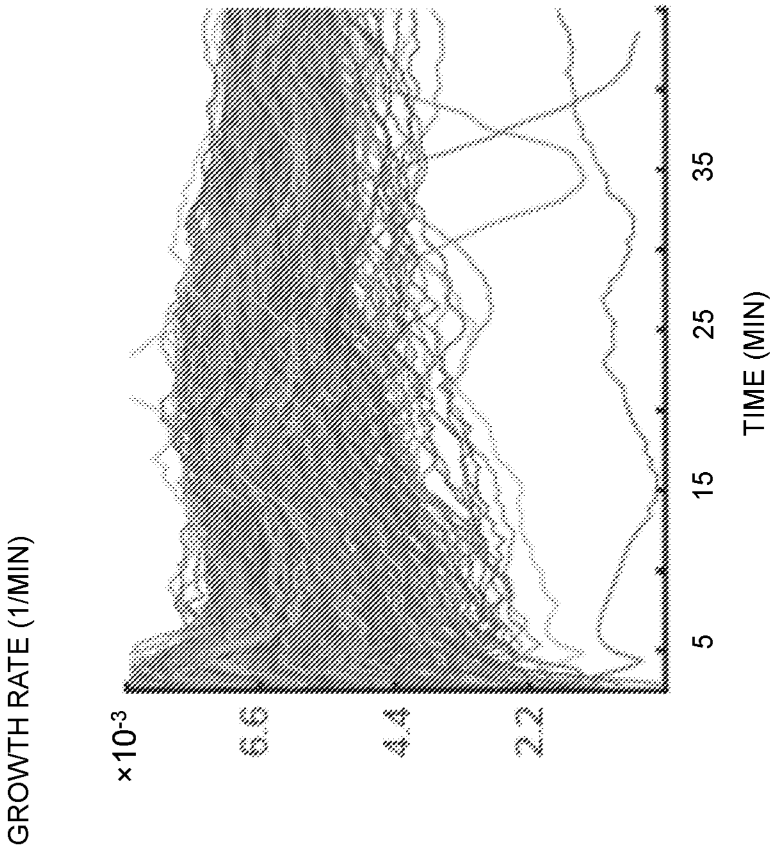

The growth rate over time typically varies between different cells. For instance, some cell types growths exponentially, whereas other grow in more periodic ways. Accordingly, the shape or form of the growth rate curve can be used to discriminate target cells from other cells and non-cell material. FIG. 20B illustrates growth rate curves of material captured in spatially defined and separated cell compartments of a microfluidic device.

Other phenotypic characteristics that vary between different cell types and between cells and non-cell material include the shape, size, color and optical density. Thus, various cell types may have different shapes, such as rod-shaped, spherical, twisted, disc-shaped, etc. Also the size, such as length and/or diameter, is a phenotypic characteristic that can be used to differentiate cells from each other and from non-cell material, such as ranging from sub-μm up to several tens of μm.

Optical density, color or other spectral properties differs between different cell types, such as depending on contents of the cells, shape of the cells, etc., and between cells and non-cell material. Thus, optical properties of the material in the spatially defined and separated cell compartments can be used to differentiate cells and non-cell material.

In order to determine or at least estimate the growth rate or determine the shape of growth rate curve the biological material and cells in the spatially defined and separated cell compartments need to be monitored at multiple time instances. However, for other target phenotype characteristics, such as cell shape, cell size, cell color and optical density it may be sufficient to monitor the biological material and cells in the spatially defined and separated cell compartments only once.

The monitoring of cells in steps S2 and S5 of FIG. 16 are thereby preferably performed using optical methods. In a particular embodiment, at least one image is taken in step S2 and/or S5 using a microscopy, such as a phase contrast microscope, connected to a camera, such as charge-coupled device (CCD) and complementary metal-oxide semiconductor (CMOS) camera, or a confocal scanning system for fluorescence, Raman imaging, Coherent Anti-stokes Raman Scattering (CARS), Stimulated Raman Scattering (SRS) and similar chemically sensitive techniques that gives spectral changes for dead and live cells. This includes measurements in one or several wavelengths with or without contrast enhancing additions to the growth media, such as chemically specific probes and dyes.

Also other techniques of monitoring cells could be used, and in particular such techniques being able to determine growth rate or cell occupation in the spatially defined and separated cell compartments. Such techniques include calorimetric methods, such as using thermopiling; electric or conductance methods, such as using coulomb or Coulter counters; etc.

Capture and thereby presence of cells at the at least one identification surface in the microfluidic device can be determined according to various embodiments. For instance, an optical analysis could be performed, such as taking a picture of at least the identification surface(s) to detect any cells captured thereon. Alternatively, various labels or tags or labelled or tagged molecules could be added and bind to the cells captured at the at least one identification surface to facilitate detection thereof. Such labels or tags include dyes; fluorescent labels/tags, such as fluorophores; chemiluminescent labels/tags; isotope labels/tags; photochromic labels/tags; fluorogen labels/tags; etc.

Figure 17:
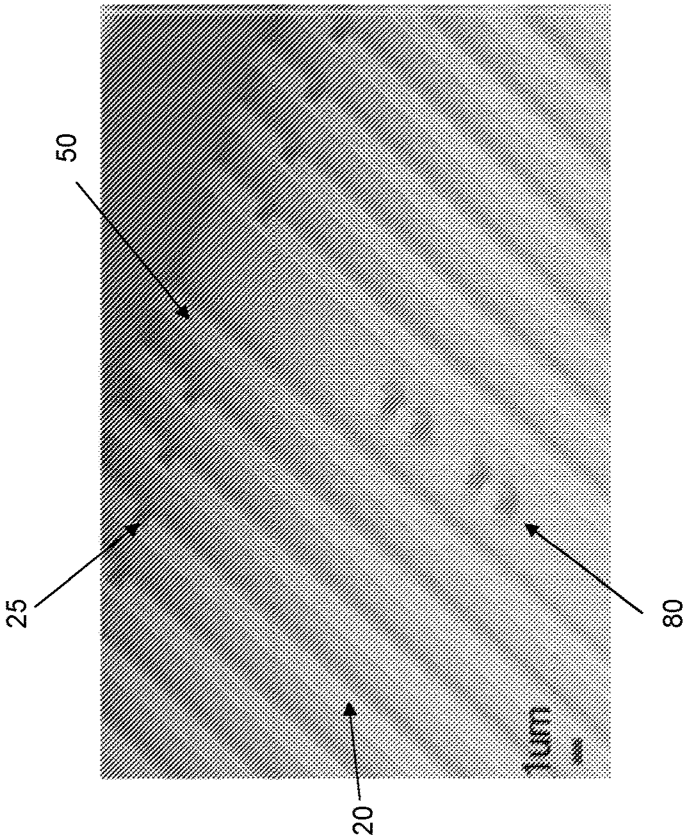
FIG. 17 is a scanning electron microscopy image showing part of the mold for a microfluidic device according to an embodiment (magnification: $11\times10^3\times$)

FIG. 17 is a scanning electron microscopy image showing part of the mold for a microfluidic device shown in in $11\times10^3\times$ magnification. The image indicates the cell channels 20 and the obstructions 25 close to the second ends of the cell channels 20. FIG. 17 also illustrate reference channels 50 that are cell channels lacking any channel obstruction. FIG. 17 further illustrates a dot barcode 80 imprinted into the substrate. The dot barcode 80 can be used to identify the spatially defined and separated cell channels 20 in the microfluidic device. Alternative individual channel identifies could be imprinted into the substrate.

Figure 18:
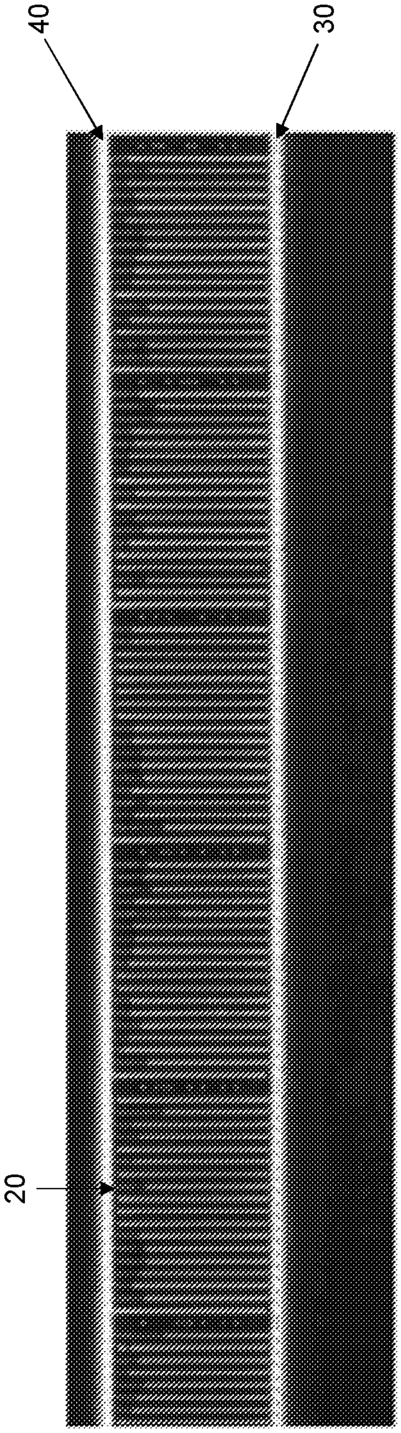
FIG. 18 is a phase contrast image of a part of a microfluidic device loaded with a biological sample.

FIG. 18 is a phase contrast image of a part of a microfluidic device loaded with a biological sample. In this image, cells present in the spatially defined and separated cell channels 20 correspond to the dark portion of the spatially defined and separated cell channels 20 facing the flow output channel 40, whereas the remaining light portions of the spatially defined and separated cell channels 20 comprise only the culture medium of the biological sample and no cells.

Figure 19:
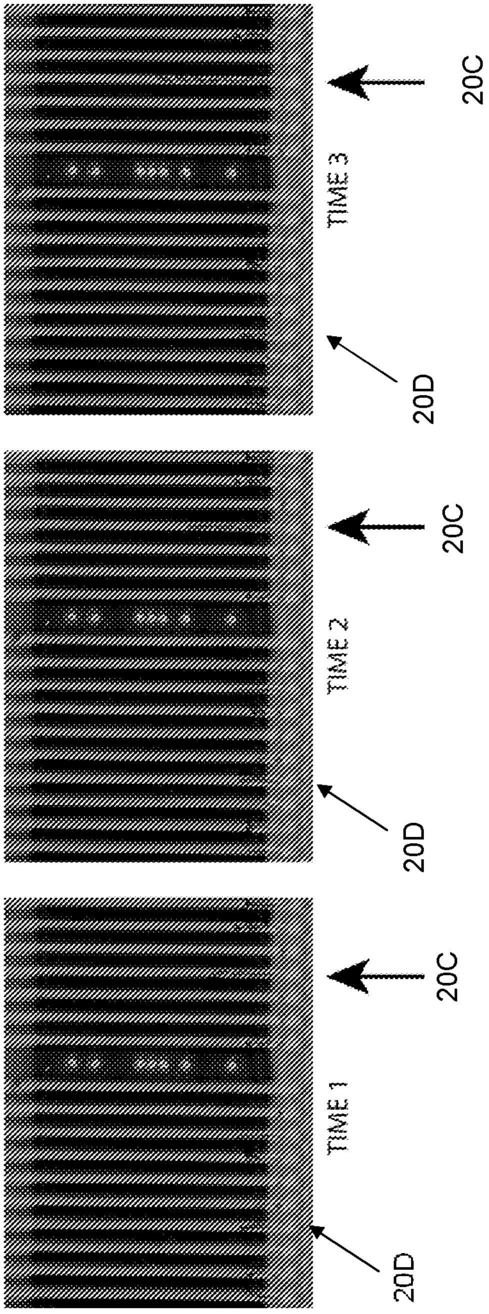
FIG. 19 are phase contrast images of a part of a microfluidic device at three different time instances following loading the microfluidic device with a biological sample.

FIG. 19 are phase contrast images of a part of a microfluidic device loaded with a biological sample taken at three different time instances. In these images, cells and non-cell material are indicated as longitudinal dark objects in the spatially defined and separated cell channels. Reference number 20C indicates a spatially defined and separated cell channel 20C that comprises cells that are growing. Hence, the number of cells present in that spatially defined and separated cell channel 20C increases when going from time 1 to time 2 and further to time 3. Reference number 20D indicates a spatially defined and separated cell channel 20D that comprises a cell not capable of growing in the particular culture medium or non-cell material. Thus, the number of cells or non-cell material in this spatially defined and separated cell channel 20D remains the same at all three time instances.

As is schematically illustrated by the three images in FIG. 19, only one of out of the shown spatially defined and separated cell channels 20C comprises cells that are viable and growing in the particular culture medium. All the remaining spatially defined and separated cell channels 20D comprise non-viable and non-growing cells or non-cell material.

FIGS. 20A and 20B show length (FIG. 20A) and growth rate (FIG. 20B) as a function of time plotted for individual cell channels of a microfluidic device. These figures indicate that there is a large difference in phenotypic characteristics of cells in a heterogeneous biological sample and that a correct and reliable characterization would benefit from an identification of species or serotype according to the embodiments.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

REFERENCES

[1] Kim et al., Miniaturized Antimicrobial Susceptibility Test by Combining Concentration Gradient Generation and Rapid Cell Culturing, *Antibiotics,* 2015, 4(4): 455-466

[2] WO 2016/007068

[3] Baltekin et al., Antibiotic susceptibility testing in less than 30 min using direct single-cell imaging, *PNAS,* 2017, 114(34): 9170-9175

[4] WO 2013/130714

The invention claimed is:

1. A microfluidic device comprising:

a substrate having a flow input channel, a flow output channel and spatially defined and separated cell channels extending from said flow input channel to said flow output channel and substantially parallel to one another, said spatially defined and separated cell channels being configured to accommodate cells, a respective first end of said spatially defined and separated cell channels being in fluid connection with said flow input channel and a respective second end of said spatially defined and separated cell channels being in fluid connection with said flow output channel; and at least one identification surface comprising immobilized affinity molecules configured to capture cells of a species or serotype or of a group of species or serotypes, wherein said spatially defined and separated cell channels comprise a respective obstruction arranged at or in connection with the respective second end of said spatially defined and separated cell channels; and said respective obstruction is operable to prevent selected cells which enter said respective first end of said spatially defined and separated cell channels from said flow input channel from passing said respective obstruction, out through said respective second end of said spatially defined and separated cell channels, and into said flow output channel, whereby said respective obstruction is operable to trap said selected cells in said spatially defined and separated cell channels, and wherein said spatially defined and separated cell channels are dimensioned to support growth of said selected cells in said spatially defined and separated cell channels.

2. The microfluidic device according to claim 1, wherein said substrate comprises said at least one identification surface.

3. The microfluidic device according to claim 2, wherein said at least one identification surface is at least one surface of said flow input channel.

4. The microfluidic device according to claim 3, wherein said flow input channel comprises:

a first end in fluid connection with a first fluid port;

a second end in fluid connection with a second fluid port; and an intermediate channel portion provided between said first end of said flow input channel and said second end of said flow input channel, wherein said respective first end of said spatially defined and separated cell channels is in fluid connection with said intermediate channel portion;

said at least one identification surface is at least one surface of said intermediate channel portion.

5. The microfluidic device according to claim 3, wherein said flow input channel comprises:

a first end in fluid connection with a first fluid port;

a second end in fluid connection with a second fluid port; and an intermediate channel portion provided between said first end of said flow input channel and said second end of said flow input channel, wherein said respective first end of said spatially defined and separated cell channels is in fluid connection with said intermediate channel portion;

said at least one identification surface is at least one surface of said flow input channel at a position between said intermediate channel portion and said second end of said flow input channel.

6. The microfluidic device according to claim 3, wherein said flow input channel comprises:

a first end in fluid connection with a first fluid port; and a channel branch dividing said flow input channel into at least a first flow input sub-channel having a second end in fluid connection with a second fluid port and a second flow input sub-channel having a second end in fluid connection with a fourth fluid port;

said respective first end of said spatially defined and separated cell channels is in fluid connection with said first flow input sub-channel; and said at least one identification surface is at least one surface of said second flow input sub-channel.

7. The microfluidic device according to claim 3, comprising at least one flow guide configured to guide at least a portion of a flow through said flow input channel over said at least one identification surface.

8. The microfluidic device according to claim 2, wherein said at least one identification surface is at least one surface of at least one spatially defined and separated cell channels.

9. The microfluidic device according to claim 2, wherein said flow output channel is in fluid connection with a third fluid port; and said at least one identification surface is at least one surface of said flow output channel.

10. The microfluidic device according to claim 1, comprising a substrate cover attached to said substrate; and said at least one identification surface is at least one surface of said substrate cover aligned with at least one of said flow input channel, at least one cell channel of said spatially defined and separated cell channels, and said flow output channel.

11. The microfluidic device according to claim 1, comprising multiple identification surfaces, wherein affinity molecules immobilized onto an identification surface of said multiple identification surfaces are configured to capture cells of a first species or serotype or of a first group of species or serotypes and affinity molecules immobilized onto other identification surface(s) of said multiple identification surfaces are configured to capture cells of a second, different species or serotype or of a second, different group of species or serotypes.

12. The microfluidic device according to claim 1, wherein said affinity molecules have affinity for at least one cell surface molecule produced by cells of said species or serotype or of said group of species or serotypes.

13. The microfluidic device according to claim 1, wherein said affinity molecules are secondary affinity molecules having affinity for primary affinity molecules having affinity for at least one cell surface molecule expressed by cells of said species or serotype or of said group of species or serotypes.

14. The microfluidic device according to claim 1, wherein said affinity molecules are antibodies configured to capture cells of said species or serotype or of said group of species or serotypes.

15. A method of characterizing cells, said method comprising:

loading a biological sample comprising cells into a microfluidic device according to claim 1 to capture cells in said spatially defined and separated cell channels;

exposing cells in said spatially defined and separated cell compartments to a test agent;

monitoring cells in said spatially defined and separated cell channels;

determining a phenotypic response of cells to said test agent based on monitoring said cells in said spatially defined and separated cell channels; and determining a species or serotype or a group of species or serotypes based on presence of cells captured by said affinity molecules immobilized onto said at least one identification surface.

16. The method according to claim 15, wherein loading said biological sample comprises loading a biological sample comprising biological material including cells into said microfluidic device to capture biological material in said spatially defined and separated cell channels;

said method further comprising:

monitoring biological material in said spatially defined and separated cell channels; and identifying a subset of said spatially defined and separated cell channels as comprising cells exhibiting at least one target phenotypic characteristic as determined based on monitoring said biological material in said spatially defined and separated cell channels, wherein exposing said cells comprises exposing biological material in said spatially defined and separated cell channels to said test agent;

monitoring said cells comprises monitoring cells in said identified subset of said spatially defined and separated cell channels; and determining said phenotypic response comprises determining a phenotypic response of cells to said test agent based on monitoring said cells in said identified subset of said spatially defined and separated cell channels.

17. The method according to claim 15, wherein said substrate comprises a first set of spatially defined and separated cell channels and a second set of spatially defined and separated cell channels;

exposing said cells comprises exposing cells in said second set of spatially defined and separated cell channels to a solution comprising said test agent and exposing cells in said first set of spatially defined and separated cell channels to said solution lacking said test agent;

monitoring said cells comprises monitoring cells in said first set of spatially defined and separated cell channels and cells in said second set of spatially defined and separated cell channels; and determining said phenotypic response comprises determining a phenotypic response of cells to said test agent based on monitoring said cells in said first set of spatially defined and separated cell channels and said cells in said second set of spatially defined and separated cell channels.

18. The method according to claim 15, wherein said test agent is an antibiotic;

monitoring said cells comprises:

measuring first relative time-dependent changes in occupation of cells in spatially defined and separated cell compartments without exposure to said antibiotic; and measuring second relative time-dependent changes in occupation of cells in spatially defined and separated cell channels with exposure to said antibiotic;

determining said phenotypic response comprises determining an antibiotic susceptibility of cells based on said first relative time-dependent changes and said second relative time-dependent changes and information of said species or serotype or said group of species or serotypes.

19. The method according to claim 15, wherein said microfluidic device comprises multiple identification surfaces;

affinity molecules immobilized onto an identification surface of said multiple identification surfaces are configured to capture cells of a first species or serotype or of a first group of species or serotypes and affinity molecules immobilized onto other identification surface(s) of said multiple identification surfaces are configured to capture cells of a second, different species or serotype or of a second, different group of species or serotypes;

each identification surface of said multiple identification surfaces being associated with a respective species or serotype or a respective group of species or serotypes; and determining said species or said group of species comprises determining a respective species or serotype or a respective group of species or serotypes based on presence of cells captured by said affinity molecules immobilized onto said multiple identification surfaces.

* * * * *